United States Patent
Dean et al.

(10) Patent No.: US 7,045,682 B1
(45) Date of Patent: May 16, 2006

(54) METHODS AND MEANS FOR MODIFICATION OF PLANT FLOWERING CHARACTERISTICS

(75) Inventors: Caroline Dean, Norwich (GB); Yaron Yakov Levy, Roskilde (DK)

(73) Assignee: Pioneer Hi-Bred International, Johnston, IA (US)

( * ) Notice: Subject to any disclaimer, the term of this patent is extended or adjusted under 35 U.S.C. 154(b) by 328 days.

(21) Appl. No.: 10/088,187

(22) PCT Filed: Sep. 13, 2000

(86) PCT No.: PCT/GB00/03525

§ 371 (c)(1),
(2), (4) Date: Sep. 25, 2002

(87) PCT Pub. No.: WO01/21822

PCT Pub. Date: Mar. 29, 2001

(30) Foreign Application Priority Data

Sep. 17, 1999 (GB) .................................. 9922071.7

(51) Int. Cl.
*C12N 15/29* (2006.01)
*C12N 15/82* (2006.01)
*C12N 5/04* (2006.01)
*A01H 5/00* (2006.01)

(52) U.S. Cl. ...................... 800/290; 800/278; 800/287; 800/320.1; 800/298; 536/23.1; 536/23.6; 435/410; 435/419; 435/320.1

(58) Field of Classification Search ............... 536/23.1, 536/23.6; 435/320.1, 468, 419; 800/278, 800/298, 290
See application file for complete search history.

(56) References Cited

FOREIGN PATENT DOCUMENTS

| WO | WO 00/44918 | 8/2000 |
|----|-------------|--------|
| WO | WO 00/46358 | 8/2000 |

OTHER PUBLICATIONS

Finnegan et al (1998, PNAS 95:5824-5829).*
Kano-Murakami et al (1993, FEBS 334:365-368).*
Bowie et al, (Science 247:1306-1310, 1990).*
McConnell et al, (Nature 411 (6838):709-713, 2001).*
Kamada et al (1992, Plant Tissue Culture Letters 9(3):206-208).*
Clarke, J.H. "Mapping *FRI*, a locus controlling flowering time and vernalization response in *Arabidopsis thaliana*"; Mol. Gen. Genet., 242: 81-89 (1994).

* cited by examiner

*Primary Examiner*—David T. Fox
*Assistant Examiner*—Stuart F. Baum
(74) *Attorney, Agent, or Firm*—Dann Dorfman Herrell and Skillman; Kathleen D. Rigaut

(57) ABSTRACT

Provided are isolated nucleic acid molecules which comprise VRN1 nucleotide sequences, which encode a polypeptide which is capable of specifically altering the vernalisation response of a plant into which the nucleic acid is introduced and expressed. Examples include cDNA and gDNA sequences (see e.g., Annex I). Also provided are variant molecules which may be derivatives or homologues (e.g., alleles, or paralogues such as RTV1), plus also complementary molecules. Corresponding polypeptides form a further part of the invention. The invention also provides methods and materials for preparing and using these molecules, e.g., in the production of plants having modified vernalisation characteristics. Also provided are methods for influencing and assessing the vernalisation phenotype of a plant.

15 Claims, 8 Drawing Sheets

Figure 7

Figure 1:
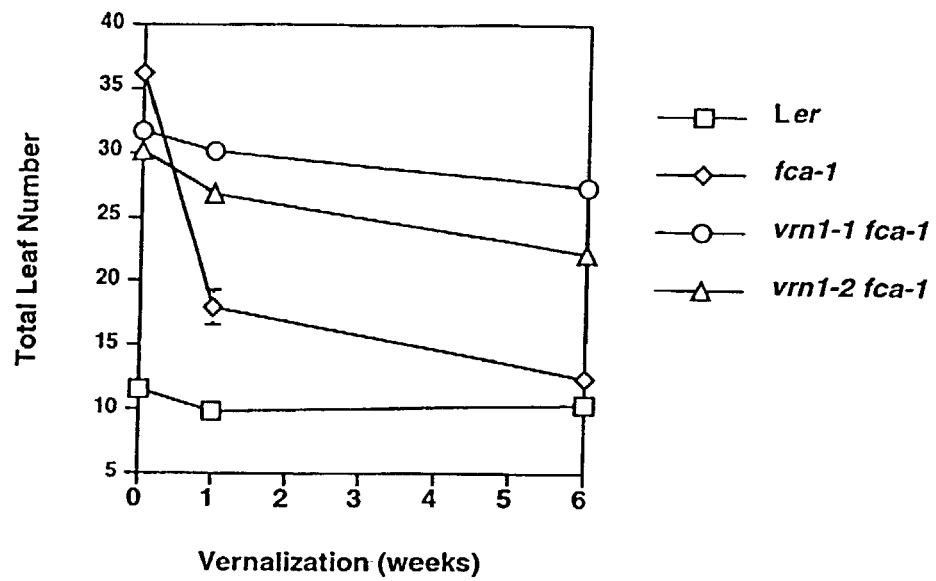
Figure 1:
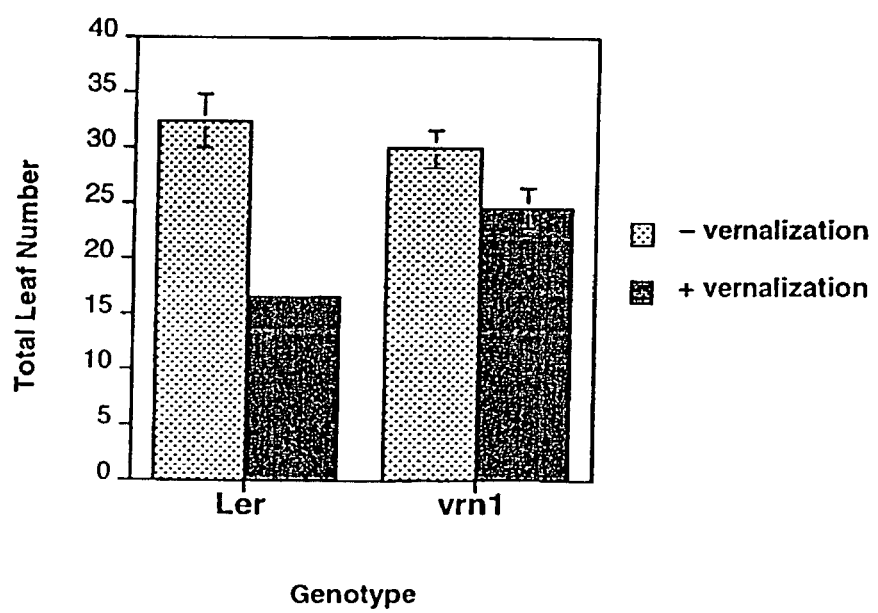

```
                                    TCTTGGGTTTGGTTGGGTCACTCTTCAGGTCAGGTGTGTAAAA    43
AAGAAAGAAAGAAAAGAGAGATTGTTGTGTTGTAACCCCTTTGACTAAAATCTAATGAACTTTTTTAACACAACA        118
AAACTCCTTCAGATCTGAAAGGGTTCTTCTTCTCTCTTAGTCTCTTTGTCCTTTTATTCTCCGTCGTCGTTTCAT        193
GATCTGACTCTCTGGTCTTCTCTTCTTCTTCTTCTTCTTCTATTTTTTCTTACTTCGTCACTGTTGTGTCTGAAC       268
                                                                    ▼
ATGCCACGCCCTTTCTTCCATAAGTTGATTTTCTCATCCACTATCCAAGAAAAACGTCTGAGGGTCCCAGATAAG        343
 M  P  R  P  F  F  H  K  L  I  F  S  S  T  I  Q  E  K  R  L  R  V  P  D  K         25
                                                        TGA in vrn1-1
TTTGTGAGTAAATTCAAGGATGAGCTTTCGGTTGCTGTTGCACTCACAGTACCTGATGGTCATGTTTGGCGTGTA         418
 F  V  S  K  F  K  D  E  L  S  V  A  V  A  L  T  V  P  D  G  H  V (W) R  V         50

GGACTAAGGAAAGCTGACAACAAAATTTGGTTTCAAGATGGTTGGCAAGAGTTTGTTGACCGTTACTCCATTCGC        493
 G  L  R  K  A  D  N  K  I  W  F  Q  D  G  W  Q  E  F  V  D  R  Y  S  I  R         75

ATTGGTTATCTTTTGATTTTTAGATATGAAGGAAACTCTGCCTTCAGCGTCTACATTTTCAATTTATCCCACTCT       568
 I  G  Y  L  L  I  F  R  Y  E  G  N  S  A  F  S  V  Y  I  F  N  L  S  H  S        100

GAGATCAATTACCATTCCACCGGTCTCATGGATTCCGCTCACAACCACTTCAAACGCGCCCGTTTGTTTGAAGAC       643
 E  I  N  Y  H  S  T  G  L  M  D  S  A  H  N  H  F  K  R  A  R  L  F  E  D        125

CTTGAAGATGAAGATGCCGAGGTCATCTTTCCTTCTTCTGTGTACCCATCACCACTTCCTGAGTCTACAGTACCA       718
 L  E  D  E  D  A  E  V  I  F  P  S  S  V  Y  P  S  L  P  E  S  T  V  P          150
                                                          ▼
GCCAACAAAGGGTATGCTAGTTCAGCCATCCAAACCTTGTTCACTGGACCAGTTAAAGCTGAAGAGCCAACGCCA       793
 A  N  K  G  Y  A  S  S  A  I  Q  T  L  F  T  G  P  V  K  A  E  E  P  T  P        175
                    G-A in vrn1-2      ▼
ACCCAAAAATACCTAAAAAGAGAGGGAGGAAGAAGAAAAATGCTGATCCTGAGGAAATAAACTCATCAGCTCCG        868
 T  P  K  I  P  K  K  R  G  R  K  K  K (N) A  D  P  E  E  I  N  S  S  A  P        200

CGAGATGATGATCCAGAGAACCGTTCAAAGTTCTACGAGAGTGCTTCTGCGAGAAAGAGAACCGTGACTGCAGAA       943
 R  D  D  D  P  E  N  R  S  K  F  Y  E  S  A  S  A  R  K  R  T  V  T  A  E        225

GAAAGAGAGAGAGCCATCAATGCAGCCAAAAACGTTCGAACCAACAAACCCTTTCTTCAGAGTGGTTCTGCGACCA      1018
 E  R  E  R  A  I  N  A  A  K  T  F  E  P  T  N  P  F  F  R  V  V  L  R  P        250
                                       ▼
TCCTATCTATACAGAGGTTGCATCATGTATCTTCCTTCTGGGTTTGCTGAGAAGTACCTAAGTGGGATCTCCGGG       1093
 S  Y  L  Y  R  G  C  I  M  Y  L  P  S  G  F  A  E  K  Y  L  S  G  I  S  G        275

TTCATCAAAGTCCAGCTTGCGGAGAAACAATGGCCTGTTCGATGTCTCTACAAAGCCGGGAGAGCCAAATTCAGT       1168
 F  I  K  V  Q  L  A  E  K  Q  W  P  V  R  C  L  Y  K  A  G  R  A  K  F  S        300

CAAGGATGGTACGAATTCACTCTAGAGAACAACTTAGGAGAAGGAGACGTCTGTGTGTTTGAGCTGCTCAGAACC       1243
 Q  G  W  Y  E  F  T  L  E  N  N  L  G  E  G  D  V  C  V  F  E  L  L  R  T        325

AGAGATTTCGTTTTGAAAGTGACAGCCTTTCGAGTCAACGAGTACGTCTGAACAAAGCATTATGGTGTGATCATT       1318
 R  D  F  V  L  K  V  T  A  F  R  V  N  E  Y  V                                   341

CTGGATTTGCAAGTACAATGTCGTGTAGGAGTATCTTAATTTAAAAACAACTAAAAAACTCTCTTCTGGTCTGTG       1393
TCATTATTGCGTCAGTGTCTCGTTTTTTCTCTCGGGTTTACTTTGTGTTATCGATGTGGATAAGTTGTTTTTACC       1468
TCATTATATATAACCTCTTGAGTGGAA                                                       1495
```

NLS (boxed), B3 DNA-binding domains (underlined),
PEST regions (doubly underlined), protein kinase C phosphorylation site (asterisks). The
positions of introns are indicated with arrowheads. The positions of the mutations in vrn1-1 and
vrn1-2 are circled.

Figure 8

```
              *         20           *         40           *         60
VRN1    MPRPFFHK---LIFSSTIQEKRLRVPDKFVSKFKDELSVAVALTVPDGHVWRVGLRKADN        57
RTV1    MPRSFFHMFNSLFLSSTQAS------------------------------GLRKANN           27

*         80           *        100           *        120
VRN1    KIWFQDGWQEFVDRYSIRIGYLLIFRYEGNSAFSVYIFN--FSHSEINYHST--GLM--D       111
RTV1    KIWFQDGWQEFVNRESIRIG----FRYKV----TVYIFQFYPPHSEINHHSSSEALMQMD        79

*        140           *        160           *        180
VRN1    SAHNHF-KRARLFEDLEDEDAEVIFPSSVYPSPLPESTVPANKGYA-SSAIQLFTGPVK       169
RTV1    SAQNQFNKRARLFEDPELKDAKVIYPSN------PESTEPVNKGYEGSTAIQSFKES-K       132

*        200           *        220           *        240
VRN1    AEEPTPTPKLPKKRGRKKKNRDPEEINSSAPRDDDPENRSKFYESASARKRTVTAEERER      229
RTV1    AEE---TPKVEKKRGRKKKNPNPEEVNSSTPGGDDSENRSKFYESASARKRTVTAEERER      189

*        260           *        280           *        300
VRN1    AINAAKTFEPTNPEFRVVLRPSYLYRGCIMYLPSGFAEKYLSGISGFIKVQLAEKQWPVR      289
RTV1    AVNAAKTFEPTNPXFRVVLRPSYLYRGCIMYLPSGFAEKYLSGISGFIKDQLGEKQWPVR      249

*        320           *        340           *
VRN1    CLYKAGRAKFSQGWYEFTLENNEGEGDVCVFELLRTRDFVLKVTAFRVNEYV              341
RTV1    CLYKAGRAKFSQGWYEFTLENNIGEGDVCVFELLRTRDFVLEVTAFRVNEYV              301
```

METHODS AND MEANS FOR MODIFICATION OF PLANT FLOWERING CHARACTERISTICS

TECHNICAL FIELD

The present invention relates generally to methods and materials for use in modifying plant characteristics, particularly the vernalization response in plants.

PRIOR ART

Plants must integrate a wide variety of environmental signals in order to maximize their reproductive success. Part of this integration must involve perception of the seasons, both to ensure the plant flowers during the correct season (for which it is adapted) and to synchronise its flowering with other members of its own species, to increase the chances of cross-fertilization. *Arabidopsis thaliana* serves as a model plant, for it exhibits responses to a wide variety of environmental stimuli that are observed in many species. Amongst other stimuli, flowering in naturally occurring strains (ecotypes) of *Arabidopsis* can be promoted by vernalization, a long cold treatment that mimics the cold of winter.

Many species of plants that grow in temperate or cooler climes have an obligate requirement for vernalization in order to flower. Such plants typically germinate in autumn, and over winter as vegetative plants, and flower in milder conditions of spring. Vernalization thus acts as a cue, to allow plants to sense the seasons, and to time their flowering to maximise their chance of reproductive success.

Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape, sugar beet, maize, sunflower, soybean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

In view of the large number of commercially important crop species which have a requirement for vernalization in order to flower, modification of this requirement (e.g. by reducing the duration of vernalization required, or changing the optimum temperature, or abrogating the requirement altogether) would be of agronomic interest.

DISCLOSURE OF THE INVENTION

The inventors have used a late flowering, vernalization responsive mutant of *Arabidopsis*, the fca mutant, as a background in which to isolate mutants that exhibit a reduced vernalization response and to identify vrn1 alleles which are responsible for this phenotype. The VRN1 gene is the first *Arabidopsis* flowering time gene to be isolated that is apparently exclusive to the vernalization promotion pathway. As discussed in more detail below, manipulation of the gene may permit the control or modification of the vernalization response of agronomically important crop species.

That VRN1 is required for a normal vernalization response is clear from the phenotype of the vrn1 mutants. Further experiments by the inventors indicate that there is a quantitative aspect to VRN1 activity. This suggests that artificially increasing or decreasing the amount of VRN1 (e.g., through overexpression or antisense suppression) may provide a tool to, inter alia fine-tune the kinetics and/or optimal temperature of the vernalization response; render plants immune to the effect of cold on flowering response; or alleviate the requirement for cold treatment altogether. In addition to quantitative manipulation, a further layer of control could be obtained by driving VRAT1 sense or anti-sense constructs using promoters that are either on all the time (constitutive); inducible upon application of a specific molecule; or which "naturally" drive expression only during a certain portion of the plant life cycle, e.g., seed maturation or late vegetative phase.

Such methods could be used to improve agronomically important crop species, for instance as follows:

(a) Extension of geographic range of elite varieties: If an elite cultivar of a crop originates from a geographic area where it has adapted to require a certain vernalization period, and it is therefore climatically-limited in its range, then fine-tuning the expression of VRN1 may permit alteration of the length and intensity of cold treatment required to achieve an optimum flowering time in new geographic areas. Two facts are noteworthy in this regard: (1) even modest alterations in vernalization response could open up huge new areas of cultivation for particular elite varieties (an analogous situation to that in which small changes in climatic conditions can alter the ecology and character of huge areas of landscape), and (2) the commercial success of elite genotypes is largely hampered by dependency on specific climatic conditions found in limited geographic areas.

(b) Shortening of vernalization period: if a winter crop can be sown and left in the ground for a shorter period than usual (i.e. a reduced vernalization time, perhaps resulting from increased- or mis-expression of VRN1) this may reduce the risk associated with severe winter weather conditions, as the crops are exposed to winter conditions for a shorter time.

(c) Extension of vegetative growth: If the crop in question is one in which the vegetative portions of the plant are the desired product (e.g., leaf vegetables, sugar beet), then preventing the plant from flowering in response to cold temperature (i.e., by rendering it less sensitive to the cold by impairing VRN1 function) would prevent diversion of valuable plant resources from the vegetative tissues to the developing reproductive tissues, thereby increasing yield.

Further experiments indicate that species other than *Arabidopsis* contain genes similar to VRN1. Additionally, homologues and/or orthologues and/or paralogues of VRN1 (such as RTV1) may also exist in *Arabidopsis* and other species. Based on the disclosure herein, such genes may be isolated without undue burden by those skilled in the art and used analogously to those disclosed herein.

These and other aspects of the present invention will now be discussed in more detail.

Thus according to one aspect of the present invention there is provided an isolated nucleic acid molecule which is capable of specifically altering the vernalisation response of a plant into which the nucleic acid is introduced.

The alteration in the vernalisation response may be assessed by comparison with a plant in which the nucleic acid has not been so introduced.

The vernalization response phenotype of plants may be investigated by examining their flowering time in response to differing durations of vernalization treatment. In the experiments below this was assessed in two ways: (1) as the total number of vegetative leaves produced prior to flowering (LN), and (2) as the time in days from the end of the vernalization treatment to the appearance of the first floral bud (FT). However any appropriate method known to those skilled in the art may be used.

Apart from the specific change in vernalisation response, it is preferred that other characteristics of the plant are substantially unchanged by the polypeptide, which is to say that the polypeptide acts specifically on this response and not more generally on flowering time characteristics or other stimuli, such as those mediated by other loci such as the FRI locus (Clarke and Dean, 1994, Mol. Gen. Genet. 242, 81–89) or the VRN2 locus (Chandler et al., 1996).

Preferably the isolated nucleic acid molecule capable of specifically altering the vernalisation response of a plant is obtainable from the VRN1 locus of a plant, more preferably from *A. thaliana*.

Nucleic acid according to the present invention may include cDNA, RNA, genomic DNA and modified nucleic acids or nucleic acid analogs (e.g. peptide nucleic acid). Where a DNA sequence is specified, e.g. with reference to a figure, unless context requires otherwise the RNA equivalent, with U substituted for T where it occurs, is encompassed. Nucleic acid molecules according to the present invention may be provided isolated and/or purified from their natural environment, in substantially pure or homogeneous form, or free or substantially free of other nucleic acids of the species of origin. Where used herein, the term "isolated" encompasses all of these possibilities. The nucleic acid molecules may be wholly or partially synthetic. In particular they may be recombinant in that nucleic acid sequences which are not found together in nature (do not run contiguously) have been ligated or otherwise combined artificially. Alternatively they may have been synthesised directly e.g. using an automated synthesiser.

Thus in one aspect of the invention, there is disclosed a nucleic acid encoding the polypeptide of FIG. 7. The VRN1 polypeptide is 341 amino acids in length and is comprised of at least three regions. Region 1 (residues 2–94 in FIG. 7) and 3 (residues 239–332) can be aligned to each other, and are related to the B3 DNA-binding domain originally found in the maize transcription factor VIVIPAROUS1 (VP1; McCarty et al., 1991). Region 2 of VRN1 (residues 95–238), which lies between the two B3 domains is not obviously related to any domain of known function, nor does it have obvious features of a transcriptional activation or repression domain. Nonetheless, region 2 does contain several provocative sequence features and motifs, including a putative nuclear localization signal (NSL), two putative PEST regions, and three RXXL motifs also associated with rapid protein degradation (Cooper et al., 1997). Interestingly, the second PEST region of VRN1 contains a potential protein kinase C (PKC) phosphorylation site (residues 176–178).

One nucleic acid encoding this polypeptide is shown in FIG. 7 from nucleotides 269–1295 inclusive (including stop codon). Other nucleic acids of the invention include those which are degeneratively equivalent to this.

A genomic sequence including the VRN1 locus is shown in Annex I. The putative cDNA sequence transcribed from this genomic sequence is shown at FIG. 7. Although this ORF has been designated the VRN1 ORF herein, it will be appreciated by those skilled in the art that the discussion hereinafter applies equally to any other ORF present in the described sequence which has the properties attributed to VRN1.

In a further aspect of the present invention there are disclosed nucleic acids which are variants of the VRN1 sequences discussed above.

A variant nucleic acid molecule shares homology with, or is identical to, all or part of the sequences discussed above.

Such variants may be used to alter the vernalisation characteristics of a plant, as assessed by the methods disclosed herein. For instance a variant nucleic acids may be include a sequence encoding a functional polypeptide (e.g. which may be a variant of the VRN1 polypeptide and which may cross-react with an antibody raised to said polypeptide). Alternatively they may include a sequence which interferes with the expression or activity of such a polypeptide (e.g. sense or anti-sense suppression of a VRN1 coding sequence).

Variants may also be used to isolate or amplify nucleic acids which have these properties (e.g. by inclusion of a sequence which is hybridisable with a VRN1 sequence.).

Generally speaking variants may be:

(i) Novel, naturally occurring, nucleic acids, isolatable using the sequences of the present invention. They may include alleles (which will include polymorphisms or mutations at one or more bases—for instance vrn1-1 (SEQ ID NO: 12) or vrn1-2 (SEQ ID NO: 13) shown in FIG. 7) or pseudoalleles (which may occur at closely linked loci to the VRN1 gene). Also included are paralogues, isogenes, or other homologous genes belonging to the same family as the VRN1 gene. Although these may occur at different genomic loci to the gene, they are likely to share conserved regions with it (see e.g. RTV1 in the Examples below). Also included are homologues of VRN1 from other plant species.

(ii) Artificial nucleic acids, which can be prepared by the skilled person in the light of the present disclosure. Such derivatives may be prepared, for instance, by site directed or random mutagenesis, or by direct synthesis. Preferably the variant nucleic acid is generated either directly or indirectly (e.g. via one or more amplification or replication steps) from an original nucleic acid having all or part of the VRN1 sequence shown in FIG. 7.

Particularly included are variants which comprise only a distinctive part or fragment (however produced) corresponding to a portion of the sequence provided. The fragments may encode particular functional parts of the polypeptide. Alternatively, the fragments may have utility in probing for, or amplifying, the sequence provided or closely related ones. Suitable lengths of fragment, and conditions, for such processes are discussed in more detail below.

Also included are nucleic acids corresponding to those above, but which have been extended at the 3' or 5' terminus.

The term 'variant' nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Homology (similarity or identity) may be assessed as set out in the Materials and Methods section in the Examples below.

Homology may be at the nucleotide sequence and/or encoded amino acid sequence level. Preferably, the nucleic acid and/or amino acid sequence shares at least about 65%, or 70%, or 80% identity, most preferably at least about 90%, 95%, 96%, 97%, 98% or 99% identity.

Homology may be over the full-length of the relevant sequence shown herein, or may be over a part of it, preferably over a contiguous sequence of about or greater than about 20, 25, 30, 33, 40, 50, 67, 133, 167, 200, 233, 267, 300, or more amino acids or codons, compared with FIG. 7.

Thus a variant polypeptide encoded by a nucleic acid of the present invention may include within the sequence shown in FIG. 7, a single amino acid or 2, 3, 4, 5, 6, 7, 8, or 9 changes, about 10, 15, 20, 30, 40 or 50 changes, or greater than about 50, 60, 70, 80 or 90 changes.

In a further aspect of the invention there is disclosed a method of producing a derivative nucleic acid comprising the step of modifying any of the sequences disclosed above, particularly the coding sequence of FIG. 7.

Changes may be desirable for a number of reasons. For instance they may introduce or remove restriction endonuclease sites or alter codon usage.

Alternatively changes to a sequence may produce a derivative by way of one or more of addition, insertion, deletion or substitution of one or more nucleotides in the nucleic acid, leading to the addition, insertion, deletion or substitution of one or more amino acids in the encoded polypeptide.

Such changes may modify sites which are required for post translation modification such as cleavage sites in the encoded polypeptide; motifs in the encoded polypeptide for phosphorylation etc. (e.g. residues 176–178 in FIG. 7). Leader or other targeting sequences (e.g. membrane or golgi locating sequences) may be added to the expressed protein to determine its location following expression if it is desired to isolate it from a microbial system.

Other desirable mutations may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the sidechain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

Particular regions, or domains, of VRN1 may have utility in their own right. For instance the B3 domains may be used to direct gene expression in a precise manner, for instance by the recognition of specific DNA sequences that represent elements in the promoters of their normal target genes. By creating fusion proteins, comprising the DNA binding domain (or domains) of VRN1, and a heterologous activation or repression domain borrowed from another protein, the expression of VRN1 target genes could be controlled. This may lead to a precise control of the expression of those genes that are normally targets of VRN1. Given that such genes, alone or in combination, ultimately control the transition to flowering (usually following vernalization), their directed expression in other conditions may provide a useful means to control flowering. Furthermore, the use of fusions based on the DNA binding domains in conventional SELEX or one-hybrid experiments may be used to reveal the target genes or DNA sequences normally bound by VRN1. Thus nucleic acids encoding these domains, or fusion proteins comprising them, form one embodiment of this aspect of the present invention.

In a further aspect of the present invention there is provided a method of identifying and/or cloning a VRN1 nucleic acid variant from a plant which method employs a sequence described above.

In one embodiment, nucleotide sequence information provided herein may be used in a data-base (e.g. of ESTs, or STSs) search to find homologous sequences, such as those which may become available in due course, and expression products of which can be tested for activity as described below.

For example, searches were conducted-using the tBLASTn Program (version 2.0 using the default parameters) available from NCBI (website: www. ncbi.nlm.nih-.gov/blast/). The 341 amino acid deduced VRN1 protein sequence was searched against all GenBank ESTs (dbEST database). Accessions are listed below which satisfied the following criteria: (1) they were expressed—all sequences are ESTs (partial), i.e., derived from mRNA; (2) they shared VRN1 domain structure—all sequences share homology with VRN1 that extends beyond either of the two B3 domains, i.e., they are not simply one of many B3-containing sequences; (3) The partial sequences share greater than or equal to 50% identity with VRN1 at the encoded amino acid level. In the light of the present invention, these partial sequences may be expected to be derived from hitherto uncharacterised VRN1-related genes.

| Species | GenBank accession: | % ID | % similarity |
|---|---|---|---|
| Medicago truncatula | AW686695 | 86 | 91 |
| Medicago truncatula | AW584452 | 82 | 91 |
| Glycine max | AW705298 | 75 | 86 |
| Gossypium hirsutum | AW187216 | 74 | 82 |
| Medicago truncatula | AW586752 | 72 | 84 |
| Gossypium arboreum | AW668373 | 69 | 85 |
| Gossypium arboreum | BE052554 | 66 | 82 |
| Gossypium arboreum | BE054829 | 66 | 78 |
| Medicago truncatula | AW685743 | 54 | 59 |
| Medicago truncatula | AW685178 | 53 | 62 |
| Medicago truncatula | BE203124 | 51 | 67 |
| Medicago truncatula | AW736517 | 51 | 65 |

(Medicago truncatula = barrel medic, Glycine max = soybean, Gossypium hirsutum = cotton, Gossypium arboreum = tree cotton).

In another embodiment the nucleotide sequence information provided herein may be used to design probes and primers for probing or amplification. An oligonucleotide for use in probing or PCR may be about 30 or fewer nucleotides in length (e.g. 18, 21 or 24). Generally specific primers are upwards of 14 nucleotides in length. For optimum specificity and cost effectiveness, primers of 16–24 nucleotides in length may be preferred. Those skilled in the art are well versed in the design of primers for use in processes such as PCR. If required, probing can be done with entire restriction fragments of the gene disclosed herein which may be 100's or even 1000's of nucleotides in length. Small variations may be introduced into the sequence to produce 'consensus' or 'degenerate' primers if required.

Such probes and primers form one aspect of the present invention.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the single stranded DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27–31, for a review).

In one embodiment, a variant in accordance with the present invention is obtainable by means of a method which includes:

(a) providing a preparation of nucleic acid, e.g. from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as are described hereinafter, (b) providing a nucleic acid molecule which is a probe or primer as discussed above, (c) contacting nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5× Denhardt's reagent, 0.5–1.0% SDS, 100 μg/ml denatured, fragmented salmon sperm DNA, 0.05% sodium pyrophosphate and up to 50% formamide. Hybridization is carried out at 37–42° C. for at least six hours.

Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_n = 81.5° C. + 16.6 \text{Log } [Na+] + 0.41 (\% \text{ G+C}) - 0.63 (\% \text{ formamide}) - 600/\#bp \text{ in duplex}$$

As an illustration of the above formula, using [Na+]=[0.368] and 50-% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Thus this aspect of the present invention includes a nucleic acid including or consisting essentially of a nucleotide sequence of complementary to a nucleotide sequence hybridisable with any encoding sequence provided herein. Another way of looking at this would be for nucleic acid according to this aspect to be hybridisable with a nucleotide sequence complementary to any encoding sequence provided herein.

In a further embodiment, hybridisation of nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of VRN1 are employed. Using RACE PCR, only one such primer may be needed (see "PCR protocols; A Guide to Methods and Applications", Eds. Innis et al, Academic Press, New York, (1990)).

Preferred primers for amplification of conserved regions of VRN1 for use as probes to obtain genomic or cDNA clones may include any of those shown in Table 3.

For instance primers S63 and S49 may be used to amplify a VRN1 genomic region including the promoter and 3' end of the gene.

Primers V7 and V2 amplify the VRN1 cDNA ORF. Primers V6 and V15 may be used to distinguish VRN1 and RTV1.

Thus a method involving use of PCR in obtaining nucleic acid according to the present invention may include:

(a) providing a preparation of plant nucleic acid, e.g. from a seed or other appropriate tissue or organ, (b) providing a pair of nucleic acid molecule primers useful in (i.e. suitable for) PCR, at least one of said primers being a primer according to the present invention as discussed above, (c) contacting nucleic acid in said preparation with said primers under conditions for performance of PCR, (d) performing PCR and determining the presence or absence of an amplified PCR product. The presence of an amplified PCR product may indicate identification of a variant.

In all cases above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

If a putative naturally occurring homologous sequence is identified, its role in vernalisation can be confirmed, for instance by methods analogous to those used in the Examples below, or by generating mutants of the gene (e.g. by screening the available insertional-mutant collections) and analyzing these for their ability to respond to vernalization, possibly in the presence and absence of other alleles such as vrn1. Alternatively the role can be inferred from mapping vrn mutants to see if the homologue lies at or close to an appropriate locus.

In a further embodiment, antibodies raised to a VRN1 polypeptide or peptide can be used in the identification and/or isolation of variant polypeptides, and then their encoding genes. Thus, the present invention provides a method of identifying or isolating VRN1 or variant thereof, comprising screening candidate polypeptides with a polypeptide comprising the antigen-binding domain of an antibody (for example whole antibody or a fragment thereof) which is able to bind said VRN1 polypeptide or variant thereof, or preferably has binding specificity for such a polypeptide. Methods of obtaining antibodies are described hereinafter.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced) Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid.

This aspect of the invention further includes an isolated nucleic acid comprising a sequence which is complementary to any of those isolated or obtained as above. The 'complement' in each case is the same length as the reference, but is 100% complementary thereto whereby by each nucleotide is base paired to its counterpart i.e. G to C, and A to T or U.

As used hereinafter, unless the context demands otherwise, the term "VRN1" is intended to cover any of the nucleic acids of the invention described above, including functional variants.

In one aspect of the present invention, the VRN1 nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus this aspect of the invention provides a gene construct, preferably a replicable vector, comprising a promoter (optionally inducible) operably linked to a nucleotide sequence provided by the present invention, such as the VRN1 gene or a variant thereof.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121–148). Suitable vectors may include plant viral-derived vectors (see e.g. EP-A-194809).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177–180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a plant cell or a microbial cell and/or induction of expression of a construct within a plant cell, by application of a suitable stimulus e.g. an effective exogenous inducer.

In a further aspect of the invention, there is disclosed a host cell containing a heterologous construct according to the present invention, especially a plant or a microbial cell.

The term "heterologous" is used broadly in this aspect to indicate that the gene/sequence of nucleotides in question (e.g. encoding VRN1) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence. Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The host cell (e.g. plant cell) is preferably transformed by the construct, which is to say that the construct becomes established within the cell, altering one or more of the cell's characteristics and hence phenotype e.g. with respect to a vernalisation response.

Nucleic acid can be introduced into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) Plant Tissue and Cell Culture, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. Plant Cell Physiol. 29: 1353 (1984)), or the vortexing method (e.g. Kindle, PNAS U.S.A. 87: 1228 (1990d) Physical methods for the transformation of plant cells are reviewed in Oard, 1991, Biotech. Adv. 9: 1–11.

Agrobacterium transformation is widely used by those skilled in the art to transform dicotyledonous species.

Recently, there has also been substantial progress towards the routine production of stable, fertile transgenic plants in almost all economically relevant monocot plants (see e.g. Hiei et al. (1994) The Plant Journal 6, 271–282)). Microprojectile bombardment, electroporation and direct DNA uptake are preferred where Agrobacterium alone is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Preferred transformation protocols for brassicas, wheat, barley and rice may be found Becker et al., 1994 and references therein. However the skilled person will appreciate that the particular choice of a transformation technology will be determined by its efficiency to transform certain plant species as well as the experience and preference of the person practising the invention with a particular methodology of choice.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g comprising the VRN1 sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., Cell Culture and Somatic Cell Genetics of Plants, Vol I, II and III, Laboratory Procedures and Their Applications, Academic Press, 1984, and Weissbach and Weissbach, Methods for Plant Molecular Biology, Academic Press, 1989.

The generation of fertile transgenic plants has been achieved in the cereals rice, maize, wheat, oat, and barley (reviewed in Shimamoto, K. (1994) Current Opinion in Biotechnology 5, 158–162.; Vasil, et al. (1992) Bio/Technology 10, 667–674; Vain et al., 1995, Biotechnology Advances 13 (4): 653–671; Vasil, 1996, Nature Biotechnology 14 page 702).

Plants which include a plant cell according to the invention are also provided. A plant according to the present invention may be one which does not breed true in one or more properties.

In addition to the regenerated plant, the present invention embraces all of the following: a clone of such a plant, seed, selfed or hybrid progeny and descendants (e.g. F1 and F2 descendants). The invention also provides a plant propagule from such plants, that is any part which may be used in reproduction or propagation, sexual or asexual, including cuttings, seed and so on. It also provides any part of these plants, which in all cases include the plant cell or heterologous VRN1 DNA described above.

Thus, one example of the above embodiment, would be to constitutively express the VRN1 protein in a transgenic plant e.g. by use of a fusion between the 35S promoter from cauliflower mosaic virus and the open reading frame from the VRN1 cDNA. Preferably this would use the binary vector SLJ1714 (Jones JDG, Shlummokov L, Carland F, English J, Scofield SR, Bishop GJ, Harrison K: Effective vectors for transformation, expression of heterologous genes, and assaying transposon excision in transgenic plants. Transgenic Research 1: 285–297 (1992)) using standard molecular techniques (Sambrook et al., 1989). In a further embodiment, inducible expression of the VRN1 protein is achieved using a gene fusions between the VRN1 open reading frame and the receptor domain of the rat glucocorticoid receptor (GR). An example of the use of this strategy to achieve inducible gene function can be found in Schena M, Lloyd A M, Davis R W: A steroid-inducible gene expression system for plant cells. Proc Natl Acad Sci USA 88(23):10421–10425 (1991) and Simon R, Igeno M I, Coupland G: Activation of floral meristem identity genes in *Arabidopsis*. Nature 384(6604): 59–62 (1996). Gene fusions can be tested, if desired, in the vrn1-2 mutant allele of *Arabidopsis* by standard *Agrobacterium* mediate transfer (Hoekema A, Hirsch PR, Hooykaas PJJ, Schilperoot A: A binary plant vector strategy based on separation of vir- and T-region of the *Agrobacterium tumefaciens* Ti-plasmid. Nature 303: 179–180 (1983)). The vernalization requirement of the different transgenic plants obtained will be analyzed compared to control (non-transformed) plants.

A further aspect of the present invention provides a method for assessing the vernalisation responsiveness of a plant, the method comprising the step of determining the presence and/or identity of a VRN1 allele therein comprising the use of a nucleic acid as described above. Such a diagnostic test may be used with transgenic or wild-type plants. The use of diagnostic tests for alleles allows the researcher or plant breeder to establish, with full confidence and independent from time consuming biochemical tests, whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants.

The method may form part of a plant breeding scheme based on selection and selfing of desirable individuals. Reliable selection for appropriate VRN1 alleles can be made in early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using established sets of markers such as RFLPs, microsatellites or SSRs, AFLPs, RAPDs etc. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a step-wise approach to fixing (making homozygous) the desired combination of flanking markers and alleles, by first identifying individuals fixed for one flanking marker and then identifying progeny fixed on the other side of the locus all the time knowing with confidence that the desirable allele is still present.

The present disclosure provides sufficient information for a person skilled in the art to obtain genomic DNA sequence for any given new or existing allele and devise a suitable nucleic acid- and/or polypeptide-based diagnostic assay. In designing a nucleic acid assay account is taken of the distinctive variation in sequence that characterizes the particular variant allele (see e.g. FIG. 7 and the allelic variations described therein).

The invention further provides a method of influencing or affecting the vernalisation response in a plant, the method including causing or allowing expression of a heterologous VRN1 nucleic acid sequence as discussed above within the cells of the plant. The method may include the use of VRN1 nucleic acid in conjunction with other genes affecting vernalisation (e.g. VRN2). As discussed in the Examples below, VRN1 and VRN2 may act in separate and partially redundant vernalization-promoting pathways.

The step may be preceded by the earlier step of introduction of the VRN1 nucleic acid into a cell of the plant or an ancestor thereof. In addition to use of the nucleic acids of the present invention for production of functional VRN1 polypeptides (thereby enhancing the vernalisation response), the information disclosed herein may also be used to reduce the activity VRN1 activity in cells in which it is desired to do so (thereby inhibiting or destroying the vernalisation response).

For instance down-regulation of expression of a target gene may be achieved using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS* USA 91, 3490–3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020. Further refinements of the gene silencing or co-suppression technology may be found in WO95/34668 (Biosource); Angell & Baulcombe (1997) The EMBO Journal 16,12: 3675–3684; and Voinnet & Baulcombe (1997) Nature 389: pg 553.

Further options for down regulation of gene expression include the use of ribozymes, e.g. hammerhead ribozymes, which can catalyse the site-specific cleavage of RNA, such as mRNA (see e.g. Jaeger (1997) "The new world of ribozymes" Curr Opin Struct Biol 7:324–335, or Gibson & Shillitoe (1997)"Ribozymes: their functions and strategies form-their use" Mol Biotechnol 7: 242–251.)

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence in the terms described above. The sequence need not include an open reading frame or specify an RNA that would be translatable.

Thus the present invention further provides the use of a variant VRN1 nucleotide sequence, or its complement, for down-regulation of gene expression, particularly down-regulation of expression of the VRN1 gene or homologue thereof, preferably in order to inhibit or suppress the vernalisation response in a plant.

Anti-sense or sense regulation may itself be regulated by employing an inducible promoter in an appropriate construct.

The present invention also encompasses the expression product of any of the coding VRN1 nucleic acid sequences disclosed and methods of making the expression product by expression from encoding nucleic acid therefore under suitable conditions, which may be in suitable host cells.

As described in the Examples, several features of VRN1 suggest that it is likely to serve as a modulator of transcription (e.g., as a "co-activator" of or "co-repressor"), or in the least as a DNA-binding protein. These features include the presence of the B3 domains; the homology of a portion of region 2 with c-myc, a transcription factor; the presence of a putative NLS, and the presence of putative signals for rapid protein degradation, which are common in transcription factors and other proteins of regulatory function (Chevaillier, 1993; Vierstra, 1996; Barnes and Gomes, 1995; Rechsteiner and Rogers, 1996; Gomes and Barnes, 1997).

The present invention also provides for the production and use of fragments of the full-length polypeptides disclosed herein, especially active portions thereof. An "active portion" of a polypeptide means a peptide which is less than said full length polypeptide, but which retains an essential biological activity. In particular, the active portion retains the ability to alter vernalization response in a plant, such as *Arabidopsis thaliana*.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Use of recombinant VRN1 protein, or a fragment (e.g the domains discussed above) thereof, as a DNA-binding protein, or more specifically a modulator of transcription, forms one aspect of the invention.

Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

Thus purified VRN1 protein, or a fragment or other variant thereof, e.g. produced recombinantly by expression from encoding nucleic acid therefor, may be used to raise antibodies employing techniques which are standard in the art. Antibodies and other polypeptides comprising antigen-binding fragments of antibodies may be used in identifying homologues from other plant species as discussed above.

Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest.

For instance, Western blotting techniques or immunoprecipitation may be used (Armitage et al, 1992, Nature 357: 80–82). Antibodies may be polyclonal or monoclonal.

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Specific binding members such as antibodies and polypeptides comprising antigen binding domains of antibodies that bind and are preferably specific for a VRN1 polypeptide or variant thereof represent further aspects of the present invention, as do their use and methods which employ them.

The above description has generally been concerned with the coding parts of the VRN1 gene and variants and products thereof. Also embraced within the present invention are untranscribed parts of the gene.

Thus a further aspect of the invention is a nucleic acid molecule encoding the promoter of the VRN1 gene, which is believed to be present in the sequence shown in Annex I (which begins at the end of the LARS1 gene).

As described in the Examples below, The VRN1 promoter region and VRN1 intron 1 were found to contain a variety of potential binding sites including low temperature response elements; binding sites for the *Arabidopsis* dehydration- and ABA-responsive gene rd22; one binding site for *Arabidopsis* Myb2, a transcription factor involved in regulation of genes responsive to water stress; H-box and TCA-1 binding sites (that may be induced by wounding and abiotic stress); and ICE-boxes (a consensus promoter element found in several cold-inducible genes).

These control elements are likely to dictate the conditions in which expression of the VRN1 transcript is obtained. For example, VRN1 may perhaps be induced by cold and/or drought treatment, or simply by application of ABA, and use of the promoter or a part thereof for induction of transcription under any of these conditions forms one aspect of the present invention.

Analysis of the upstream region will reveal control regions for gene expression including control regions common to many genes (i.e TATA and CAAT boxes) and other control regions, usually located from 1 to 10,000, such as 1 to 1000 or 50 to 500 nucleotides upstream of the start of transcription. To find minimal elements or motifs responsible for regulation, restriction enzyme or nucleases may be used to digest a nucleic acid molecule, or mutagenesis may be employed, followed by an appropriate assay (for example using a reporter gene such as luciferase) to determine promoter activity. The control region may also be mutated to identify specific subregions responsible for transcriptional control. This may be achieved by a number of techniques well known in the art as such, including DNase protection footprint assays, in which the control region is brought into contact with an extract from a cell in which the VRN1 gene is actively expressed, and the regions of the control region which bind factors in that extract is determined.

Nucleic acid comprising these elements or motifs forms one part of the present invention.

"Promoter activity" is used to refer to ability to initiate transcription under appropriate conditions e.g. optionally in the presence of an inducer. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction.

Those skilled in the art are well aware of a multitude of possible reporter genes and assay techniques which may be used to determine promoter activity. Any suitable reporter/assay may be used and it should be appreciated that no particular choice is essential to or a limitation of the present invention. Also provided is a nucleic acid construct, preferably an expression vector, including the VRN1 promoter (or active fragment or variant thereof able to promote transcription) operably linked to a heterologous gene, e.g. a coding sequence, which is preferably not the coding sequence with which the promoter is operably linked in nature.

The invention will now be further described with reference to the following non-limiting Figures and Examples. Other embodiments of the invention will occur to those skilled in the art in the light of these.

FIGURES & SEQUENCE ANNEXES

FIG. 1: Vernalization phenotype of vrn1 mutant under LDs and SDs; vernalization phenotype of vrn1-1 allele compared to vrn1-2 allele.

Figure 2:
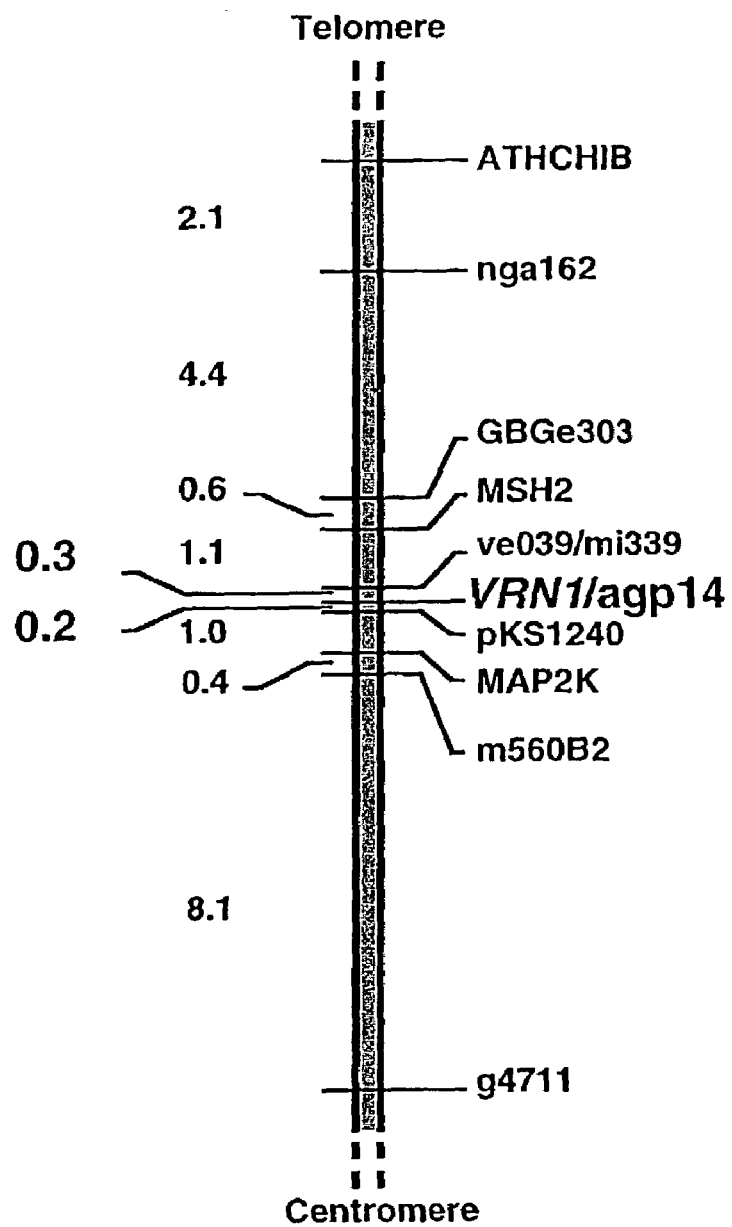

FIG. 2: Genetic map of the position of VRN1 on chromosome III in relation to markers used for mapping. The markers (shown on right) were scored on a population of 494 F2 plants from a cross between vrn1-1 fad×fca-10. The distance in cM between each marker is shown on the left.

Figure 3:
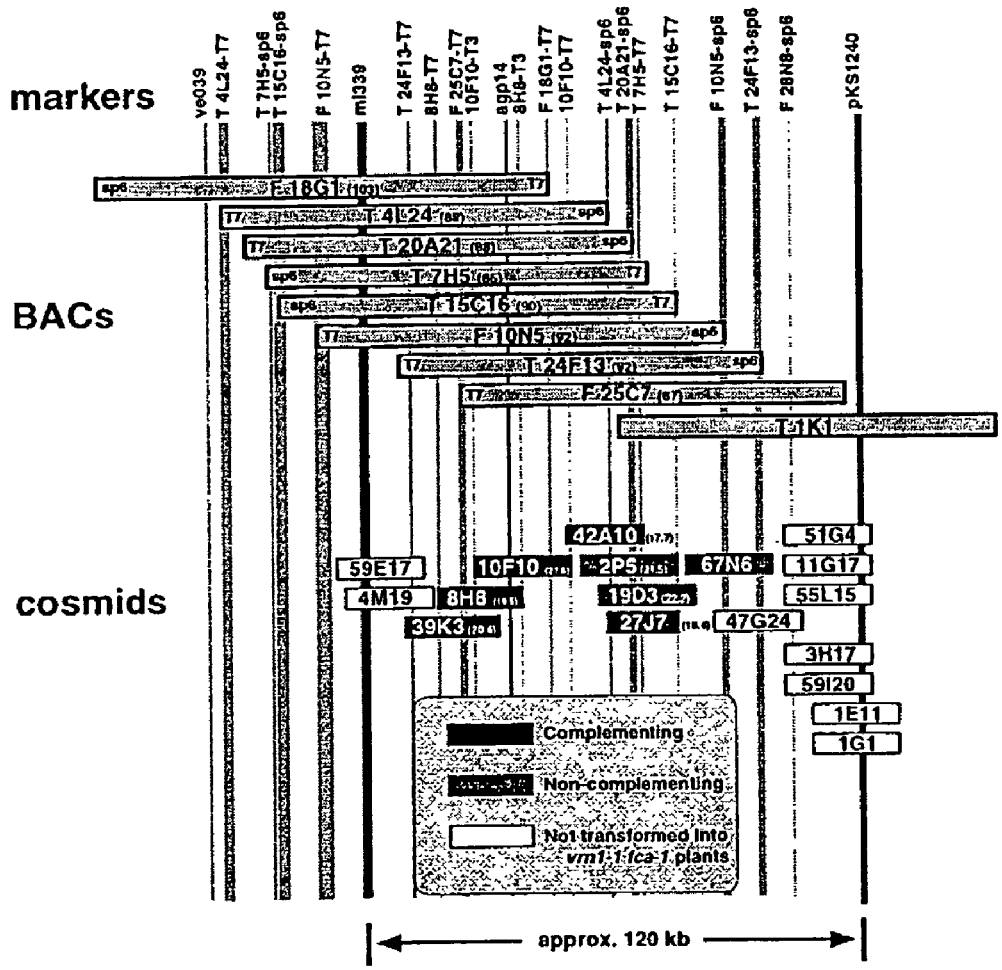

FIG. 3: Physical map of the region containing VRN1.

Figure 4:
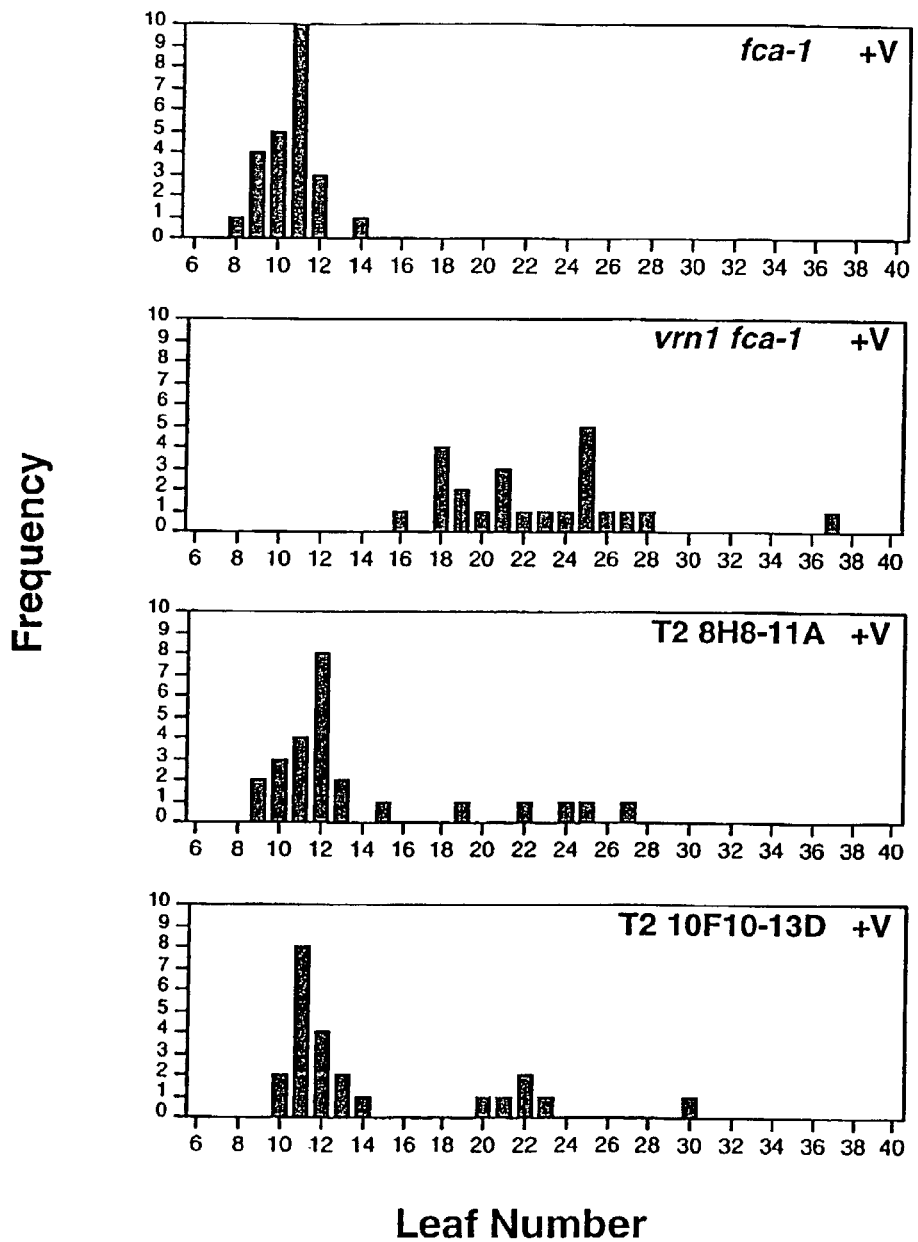

FIG. 4: Complementation of the vrn1-1 mutant phenotype by cosmids 8H8 and 10F10. Following vernalization. fca-1 plants flower early and vrn1-1 fca-1 plants flower late. Representative T2 lines in which cosmid 8H8 or 10F10 has been transformed in vrn1-1 fca-1 plants show the expected ratio (approx. 3:1) of early-to-late flowering plants.

Figure 5:
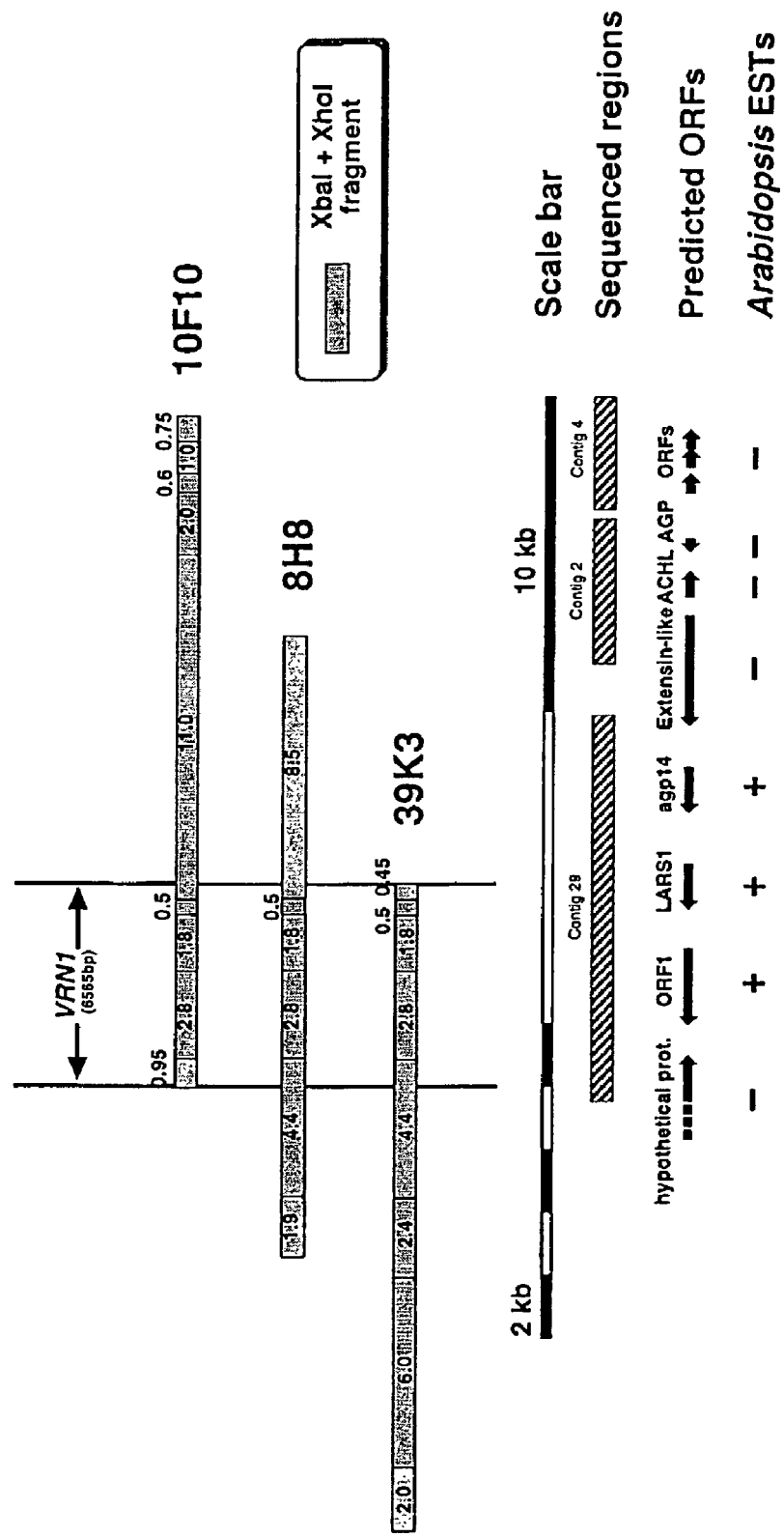

FIG. 5: Sequenced region, and predicted ORFs in the vicinity of VRN1. Overlap between cosmids was initially determined by XbaI+XhoI digestion and Southern blotting. Sequencing of cosmid DNA confirmed these results and revealed the complementing region as 6565 bp. ORF1 was subsequently shown to be VRN1.

Figure 6:
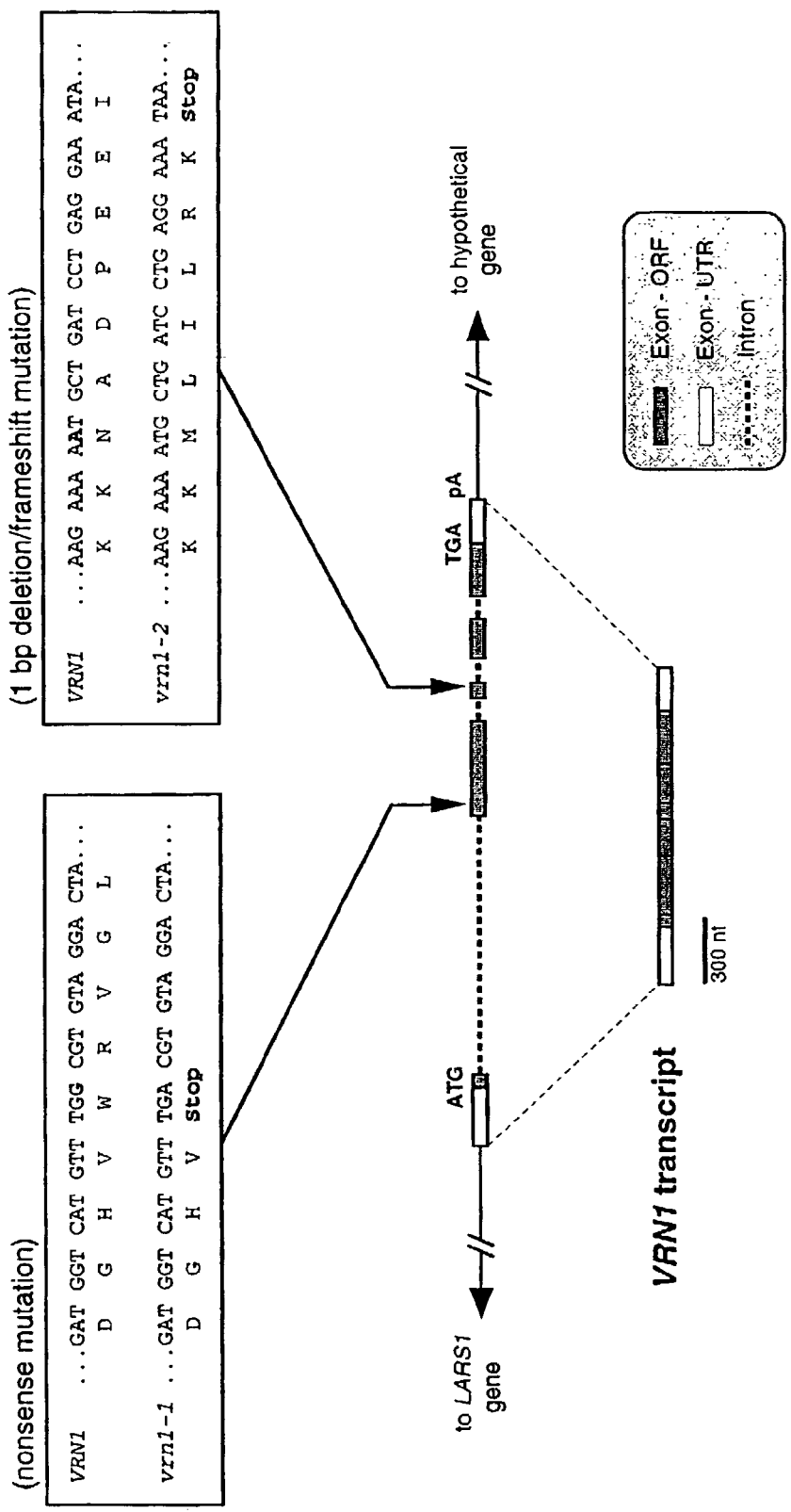

FIG. 6: Structure of the VRN1 gene and transcript, and positions of the vrn1-1 and vrn1-2 mutations. SEQ ID NOs: 2 and 3 (top) and SEQ ID NOs: 4 and 5 (bottom) are shown in the nonsense mutation box and SEQ ID NOs: 6 and 7 (top) and SEQ ID NOs: 8 and 9 (bottom) are shown in the 1 bp deletion/frameshift mutation box.

FIG. 7: The putative VRN1 transcript and its deduced amino acid sequence (SEQ ID NO: 10; the amino acid sequence is SEQ ID NO: 11).

FIG. 8: Alignment of VRN1 (SEQ ID NO: 11) and RTV1 (SEQ ID NO: 48).

Annex I: this shows contig 29 [bp 1501–6500]) derived from Ler VRN1 genomic DNA. The VRN1 promoter is present in the region between about nucleotides 1 to 1879.

EXAMPLES

Example 1

Isolation of the vrn1 Mutants

The vrn1 mutation was selected from mutagenized populations of *Arabidopsis thaliana* (L.) Heynh (Landsberg erecta ecotype) plants on the basis of its impairment of the acceleration of flowering following a six week cold treatment (vernalization).

Mutants were subsequently analyzed for flowering time in the absence of vernalization in order to confirm that the induced defect was specific to the process of vernalization and not due to a general late-flowering mutation (Chandler et al., 1996).

Two recessive alleles of vrn1 have been identified: (1) vrn1-1 was isolated by mutagenising fca-1 seeds with EMS, as described (Chandler et al., 1996), and (2) vrn1-2 was isolated by mutagenising fca-1 seeds with gamma irradiation. The vrn1-1 fca-1 line used here was backcrossed to fca-1 two times prior to genetic mapping. Subsequently, vrn1-1 fca-1 was further backcrossed to fca-1 (six times in total) and vrn1-2 fca-1 was backcrossed two times in total.

Example 2

Characterization of the vrn1 Phenotype

The vernalization dose-response phenotype of vrn1 mutant plants was investigated by examining their flowering time in response to differing durations of vernalization treatment. Flowering time was measured in two ways: (1) as the total number of vegetative leaves produced prior to flowering (LN), and (2) as the time in days from the end of the vernalization treatment to the appearance of the first floral bud (FT). In all experiments these two measures were positively correlated, so only LN is given in order to more easily facilitate comparison between experiments.

Two types of experiment were conducted: (1) a dose-response analysis of vrn1-1 fca-1 and vrn1-2 fca-1 examined under long day (LD) growth conditions (FIG. 1A), and (2) the effect of 6 weeks of vernalization on vrn1-1 in the absence of fca-1 examined under short day (SD) growth conditions (FIG. 1B). In the LD experiment shown in FIG. 1A, with no vernalization (0 weeks), both vrn1-1 fca-1 and vrn1-2 fca-1 mutant plants flowered very slightly earlier compared to the parental fca-1 controls, although in other experiments vrn1-1 fca-1 and vrn1-2 fca-1 mutant plants flowered at approximately the same time as fca-1 with no vernalization. In contrast, following vernalization, fca-1 plants showed a marked reduction in leaf number (≈66% after 6 weeks of vernalization), while vrn1-1 fca-1 and vrn1-2 fca-1 mutant plants showed a much reduced response (≈14% and ≈27% after 6 weeks of vernalization, respectively). Therefore, both alleles of vrn1 are dramatically impaired in their response to vernalization, with vrn1-1 being more severe than vrn1-2.

In the SD experiment shown in FIG. 1B, the wild type Ler plants exhibited a ≈49% reduction in leaf number after a vernalization treatment of six weeks compared to unvernalized plants. However, vrn1-1 mutant plants showed only a ≈18% reduction under the same conditions. In addition, this experiment shows that the phenotype of vrn1-1 does not depend on the presence of the fca-1 mutation or on long day photoperiods. vrn1-1 was also combined with other late flowering, vernalization-responsive mutations (fve-1, ld-3, fwa-1, fe-1, fpa-2, and ft-1) and was shown to impair the vernalization response of these mutants as well (Chandler et al., 1996).

Example 3

Genetic Mapping of VRN1

The VRN1 gene was initially mapped to the top arm of chromosome III, between RLFP markers mi207 and mi339, using a relatively small F2 population (77 plants) derived from a cross between vrn1-1 fca-1 and fca-10, as described (Chandler et al., 1996). A larger population (494 F2 plants) derived from the same cross was then used to finely map the position of VRN1 (FIG. 2). The dearth of available genetic markers in this region necessitated the development of several new genetic markers that were polymorphic between the Ler and Ws ecotypes (Table 1). As a first step, two markers flanking VRN1, ATHCHIB (SSLP) and g4711 (CAPS) were used to screen the population for recombinants in this ≈18 cM interval. Approximately 170 recombinant chromosomes were identified. Next, the markers indicated in FIG. 2 were used with these recombinants to define the position of VRN1 to the ≈0.5 cM interval between mi339 (2 recombinants to the north) and pKS1240 (one recombinant to the south). The CAPS marker agp14, corresponding to a dioxygenase gene, was genetically inseparable from VRN1 (FIG. 2).

Example 4

Physical Mapping of VRN1

The interval between mi339 and pKS1240 fell in a gap between Contig 3 and Contig 4 of the CIC YAC coverage of chromosome III (Camilleri et al., 1998) so therefore no physical map data was available. Initially, an attempt was made to fill the gap using YAC clones other than those derived from the CIC library (i.e., yUP, EW, and EG), but this genomic region was apparently not represented in any of these libraries. Therefore, a physical map of the interval was constructed using IGF (Mozo et al., 1998) and TAMU (website address: genome-www.stanford.edu/*Arabidopsis*/ww/Vol2/choi.html) BAC clones. Marker mi339 was used to screen the BAC libraries and to initiate a walk towards pKS1240. BAC contigs (FIG. 3) were assembled by hybridizing BACs to end probes developed by iPCR (Table 2) and by using publicly available BAC end sequence data (from TIGR; website address www.tigr.org/tdb/at/atgenome/bac_end_search/bac_end_search.htm 1) as the basis for designing oligonucleotide primers for PCR (Table 2). The size of individual BAC clones was determined by hexagonal pulsed-field gel electrophoresis (Maule, 1997). The ≈0.5 cM interval between mi339 and pKS1240 containing the VRN1 gene was therefore found to correspond to ≈120 kb of genomic DNA.

In preparation for cosmid complementation experiments, a Ler genomic library in the cosmid 04541 binary vector (Macknight et al., 1997) was initially screened using the following probes: BAC T24F13, mi339, agp14, and pKS1240. Putative positive clones were verified on Southern blots and the overlap between individual cosmids determined by either hybridization with DNA probes or with PCR primers designed from BAC- and cosmid- end sequence data (Table 2). The insert sizes of individual cosmid clones was determined by digestion with XbaI+XhoI followed by standard agarose gel electrophoresis using lambda DNA cut with HindIII as a standard. A complete cosmid contig was generated over the ≈120 kb region (FIG. 3).

Example 5

Cosmid Complementation of the vrn1 Phenotype

Eight cosmids (39K3, 8H8, 10F10, 42A10, 2P5, 19D3, 27J7, 67N6) centered around the marker agp14 were transformed into vrn1-1 fca-1 plants by *Agrobacterium tumefaciens*-infection of root tissue (Hooykaas, 1989). In order to test if any of these cosmids rescued the mutant phenotype of vrn1-1 fca-1, T2 seed (from individual T1 kanamycin resistant transformants) was sown on soil and vernalized for 5 weeks. Seedlings were then transferred to LD conditions, and pricked out into individual compartments of divided trays after about a week of growth. The total leaf number prior to flowering was determined, and cosmids were scored as complementing if the segregation ratio of early to late plants (compared to fca-1 and vrn1-1 fca-1 controls) was approximately 3:1 or greater. Eight independent lines containing cosmid 8H8, eight independent lines containing cosmid 10F10, and three independent lines containing cosmid 39K3 were found to rescue mutant phenotype of vrn1-1 fca-1. Lines containing the other five cosmids did not complement the vrn1-1 phenotype (FIG. 3). Analysis of the flowering time segregation in typical 8H8 and 10F10 complementing lines is shown in FIG. 4. The presence of each cosmid in complementing lines (T2 plants) was confirmed by a cosmid-specific diagnostic PCR, comprising an insert specific primer 8H8DIAG1 (ACCTGCTTCTGC-CAACCGCTC; SEQ ID NO: 14) and 10F10DIAG1 (AGT-TCGCTCTTGCTGTTTTTTTTCCC; SEQ ID NO: 15)(corresponding to a portion of the Ler genomic DNA) and a primer BACT 7U (CCTCTTCGCTATTACGCCAG; SEQ ID NO: 16) present in the cosmid vector (see "cosmid complementation" under "materials and methods" below).

PCR, comprising an insert specific primer 8H8DIAG1 (ACCTGCTTCTGCCAACCGCTC) and 10F10DIAG1 (AGTTCGCTCTTGCTGTTTTTTTTCCC)(corresponding to a portion of the Ler genomic DNA) and a primer BACT 7U (CCTCTTCGCTATTACGCCAG) present in the cosmid vector (see "cosmid complementation" under "materials and methods" below).

Example 6

Analysis of Genomic DNA Corresponding to the Complementing Region (a) Sequencing of Cosmid DNA The region of chromosome III corresponding to the cosmid contig surrounding VRN1 (FIG. 3) had apparently not previously been sequenced. Therefore the insert DNA from cosmids 8H8, 10F10, and 39K3 (derived from Ler genomic DNA) was sequenced by a combination of primer walking and shotgun strategies (Table 3), resulting in three contigs of sequence (FIG. 5). The total amount of new Arabidopsis genomic sequence obtained was 20950 bp.

(B) Identification of Candidate ORFs in Genomic Sequence

As new genomic sequence data was obtained it was analyzed in several ways in order to identify potential open reading frames (ORFs) and genes. Firstly, homology searches were carried out using the BLAST and FASTA computer programs available from the Arabidopsis thaliana Database (AtDB; website address: genome- www.stanford-.edu/Arabidopsis/seqtools.html) and National Center for Biotechnology Information (NCBI; website address: www.ncbi.nlm.nih.gov/BLAST/). Using these programs, genomic sequence in the VRN1 region was compared (1) the Arabidopsis EST database, and (2) the database of all non-redundant Genbank sequences. Secondly, searches were carried out using the NetPlantGene website address: www.cbs.dtu.dk/NetPlantGene.html), BCM Gene Finder website address: (dot.imgen.bcm.tmc.edu:9331/gene-finder/ gf.html), and GENESCAN website address: genomic.stan- ford.edu/GENSCANW.html) computer programs which are designed to recognize features of eukaryotic genes, such as intron-exon boundaries, ORFs and polyadenylation signals. The results of these analyses are summarized in FIG. 5 ("Predicted ORFs"). The sequenced region (contigs 29, 2, and 4) was found to contain =8 potential genes. Three of these, agp14, LARS1, and ORF1 (later identified as VRAT1) were represented by ESTs in the GenBank EST database.

Example 7

Identification of the vrn1-1 and vrn1-2 Mutations and Determination of the VRN1 Gene Structure (A) Finding Mutations in vrn1 Mutant Plants The three cosmids which rescued the vrn1-1 fca-1 mutant phenotype (8H8, 10F10, 39K3) were subjected to restriction analysis using XbaI and XhoI (FIG. 5) and the region of overlap between these three cosmids found to be =6.5 kb. The ORF analysis indicated that this 6.5 kb interval con- tained the 3' end of the LARS1 gene (a dioxygenase closely related to agp14), the 3' end of a hypothetical gene of unknown function, and the entire structure of another gene, "ORF1" (FIG. 5).

In order to determine if either LARS1 or ORF1 corre- sponded to VRN1, a search for the presence of mutations in these genes in vrn1-1 fca1 and vrn1-2 fca-1 mutant plants was carried out. PCR primers initially used in the sequenc- ing of cosmid DNA (Table 3) were now used to amplify products from vrn1-1 fca-1 and vrn1-2 fca-1 genomic DNA. Overlapping products that encompassed the entire predicted ORF of LARS1 and ORF1 were sequenced on both strands and compared to the Ler-derived cosmid sequence for the presence of differences corresponding to mutations. No mutations were found in the LARS1 gene, but in ORF1, a 1bp nonsense mutation was found in vrn1-1 fca-1-derived DNA and a 1bp deletion was found in vrn1-2 fca-1-derived DNA (FIG. 6). Each of these putative mutations were then confirmed by sequencing four more independent PCR prod- ucts on both strands. The effect of the vrn1-1 and vrn1-2 mutations on the encoded VRN1 protein is described in Example 8.

(B) Determining the Structure of the VRN1 Gene

The structure of the VRN1 gene and putative transcript was determined by a combination of (1) RT-PCR analysis, (2) 3'-RACE analysis, and (3) analysis of partial cDNA clones represented in the GenBank Arabidopsis EST data- base (Table 4).

These techniques revealed the sequence of the VRN1 transcript and by comparing this sequence with the VRN1 genomic sequence, the intron/exon boundaries were deter- mined (FIG. 6, FIG. 7). The results obtained by these approaches were all in agreement, i.e., the intron-exon boundaries and point of polyadenylation determined by RT-PCR and 3'-RACE were identical to those determined through analysis of EST clones corresponding to VRN1 cDNA, although the 5' transcription start site of the VRN1 gene was not definitively determined by the experiments. Within the putative VRN1 transcript (FIG. 7), the Ler- derived sequence obtained by RT-PCR and the Columbia- derived sequence obtained by the sequencing of EST clones were 100% identical.

The VRN1 gene is comprised of 5 exons and covers =3.0 kb of genomic DNA from the putative transcription start to the point of polyadenylation (see Annex I). Introns 2, 3, and 4 are a typical size for an Arabidopsis gene (=100 bp), while intron 1 is quite large: =1.2 kb (FIG. 6). The 5- and 3-UTR of the VRN1 transcript are also somewhat larger than average: =270 and =200 bp, respectively (FIGS. 6, 7).

The VRN1 promoter region (from end of LARS1 gene to VRN1 translation initiation codon) and VRN1 intron 1 were analyzed for binding sites of known plant transcription factors and known promoter elements using the Web Signal Scan program and PLACE database website address: (ww- w.dna.affrc.go.jp/htdocs/PLACE/signalscan.html). These regions of VRN1, which may potentially specify the expres- sion of the VRN1 gene, were found to contain the following potential binding sites: (1) two low temperature response elements (LTREs; also known as CRT/DREs), found in several cold-induced genes from Arabidopsis, Brassica napus, and barley and bound by the transcription factor CBF1 (Baker et al., 1994; Stockinger et al., 1997; Jiang et al., 1996; Nordin et al., 1993), (2) three binding sites for the Arabidopsis dehydration- and ABA-responsive gene rd22 (Abe et al., 1997), (3) one binding site for Arabidopsis Myb2, a transcription factor involved in regulation of genes responsive to water stress (Urao et al., 1993), (4) one H-box and three TCA-1 binding sites, promoter elements found in several tobacco, barley, and bean (P. vulgaris) genes that are induced by wounding and abiotic stress (Loake et al., 1992;

Mhiri et al., 1997; Goldsbrough et al., 1993), and (5) three ICE-boxes, a consensus promoter element found in several cold-inducible genes (G. J. Warren, unpublished). It is interesting that control elements for both cold- and drought-inducible genes are present within the VRN1 promoter and intron 1, as these conditions are known to induce several genes involved in acclimation to freezing temperatures (Thomashow, 1994), and ABA signaling is involved (Gilmour and Thomashow, 1991). These control elements are likely to dictate the conditions in which expression of the VRN1 transcript is obtained. For example, VRN1 may perhaps be induced by cold and/or drought treatment, or simply by application of ABA.

Taken together, the presence of mutations within ORF1 (the only predicted gene that was completely contained within the complementing region) in genomic DNA derived from vrn1-1 and vrn1-2 mutant plants confirmed that ORF1 corresponds to the VRN1 gene.

This may be readily confirmed by introduction of the ORF (in sense and antisense) into *Arabidopsis* (cf. Example 5 above). Constructs may be based on the pGreen0029 vector which drives expression of the cloned in gene with a double 35S promoter and terminator derived from CAMV. This vector, and how to obtain it, is discussed in detail in WO 99/27120 (Plant Bioscience Limited).

(1) Genomic sense construct: the unspliced (genomic) VRN1 ORF in the sense orientation in order to produce high levels of functional VRN1 product. This construct will be put into vrn1-1 fca-1 and vrn1-2 fca-1 plants.

(2) cDNA sense construct: the spliced (cDNA) VRN1 ORF in the sense orientation in order to produce high levels of functional VRN1 product. This construct will be put into vrn1-1 fca-1 and vrn1-2 fca-1 plants.

(3) cDNA antisense construct: the spliced (cDNA) VRN1 ORF in the antisense orientation in order to repress the normal expression of VRN1 and diminish the amount of functional VRN1 product. This construct will be put into fca-1 and Ler plants.

As an alternative to a constitutive promoter, it may be desirable to use an inducible promoter, such as one which is controlled by application of the molecule dexamethasone.

Example 8

Analysis of the Putative Protein Encoded by the VRN1 Gene

The deduced amino acid sequence of VRN1 (FIG. 7) was compared with the entire GenBank database (NCBI) using the BLASTP and TBLASTN programs.

(A) VRN1: Domain Structure, Sequence Features, and Similarity to Other Known and Hypothetical Sequences The VRN1 gene encodes a putative protein of 341aa (calculated MW=39278 Da) that is basic (pI=9.1), and is comprised of at least three regions. Region 1 (residues 2–94 in FIG. 7) and 3 (residues 239–332) which are homologous to each other and are related to the B3 DNA-binding domain originally found in the maize transcription factor VIVIPA-ROUS1 (VP1; McCarty et al., 1991). Domains similar to the B3 domain of VP1 have subsequently been found in several *Arabidopsis* transcription factors or putative transcription factors such as ABI3 (the *Arabidopsis* orthologue of maize VP1, (Giraudat et al., 1992), auxin response factors (Ulmasov et al., 1997), IAA response factors (Kim et al., 1997; Abel et al., 1994; Guilfoyle et al., 1998), FUSCA3 (Luerssen et al., 1998), and RAVs (Kagaya et al., 1999). Several of these proteins have been shown to bind DNA in sequence-specific manner via their B3 domain (e.g., Kagaya et al., 1999; Suzuki et al., 1997; Ulmasov et al., 1997).

The B3 DNA-binding domain appears to be specific to plants (Suzuki et al., 1997), and analysis of translated nucleotide sequences (i.e., hypothetical proteins) in the GenBank databases has revealed at least 22 *Arabidopsis* sequences that contain B3 domains, as well as EST sequences from several other plant species such as *Brassica oleracea*, hybrid aspen (*Populus tremula×P. tremuloides*), and tomato. While VRN1 contains two B3 domains, most characterized and hypothetical amino acid sequences were found to contain only one B3 domain, and some were found to contain more than two. The B3 domain appears to be "defined" by a number of conserved positions (results not shown) rather than sequence identity over the whole domain. Therefore, BLAST scores between the sequences shown tested are only marginally significant (on the order of $10^{-6}$ to $10^{-1}$). The C-terminal portion of the B3 domain is more conserved than the N-terminal portion.

Phylogenetic analysis of B3 domains (results not shown) using the Clustal method suggests that *Arabidopsis* B3-containing proteins fall into several groups: (1) ABI3- and FUSCA3-like B3s, (2) auxin response factor- (ARFs) and IAA-inducible protein-like B3s, (3) RAV1-like B3s, and (4) at least four uncharacterized groups, which include the VRN1-like B3s. It is likely that through evolution the B3 domain has been recruited in different ways by proteins involved in diverse plant processes.

Region 2 of VRN1 (residues 95–238), which lies between the two B3 domains (FIG. 7), is not obviously related to any domain of known function, nor does it have obvious features of a transcriptional activation or repression domain. Nonetheless, region 2 does contain several sequence features and motifs of interest, including a putative nuclear localization signal (NSL), two putative PEST regions (identified using the PEST Sequence Utility (website address: www.lif.ic-net.uk/LRITu/projects/pest/) based on Rechsteiner and Rogers, 1996; Rogers et al., 1986), and three RXXL motifs also associated with rapid protein degradation (Cooper et al., 1997) (FIG. 7). Interestingly, the second PEST region of VRN1 contains a potential protein kinase C (PKC) phosphorylation site (residues 176–178 in FIG. 7). There are several examples in the literature for regulation of the cellular "lifespan" of proteins by phosphorylation of PEST regions (e.g., McKinsey et al., 1997; Koepp et al., 1999; Yaglom et al., 1996; Marchal et al., 1998; Liu et al., 1997). For example, in the case of IkB, stimulation of cell surface receptors by cytokines initiates a signal transduction cascade that phosphorylates IkB at two specific serine residues in the PEST region, triggering the polyubiquitination of nearby lysine residues and ultimately proteolysis (McKinsey et al., 1997; Laney and Hochstrasser, 1999).

Analysis of the physiochemical characteristics of VRN1 suggest that the two B3 domains are basic (average pI=9.5) and slightly hydrophobic in character, while region 2 is slightly acidic (pI=6.3) and somewhat hydrophilic and therefore likely to be on the surface of the molecule and exposed to the aqueous environment. Interestingly, unlike the B3 domains which appear to be specific to plants, BLAST searches against GenBank (NCBI) with region 2 of VRN1 picked up no significant hits from plants (except for RTV1, see below) but did reveal weak homology between the N-terminal portion of region 2 (residues 109–167) and a region of the vertebrate proto-oncogene transcription factor c-MYC (Schmidt, 1999).

Furthermore, this region of c-myc lies in the linker between the DNA-binding domain and the transcriptional activation domain (Kerkhoff and Bister, 1991; Classon et al., 1993) and is not required for the oncogenic transformation activity of the protein (Stone et al., 1987). By analogy, this portion of region 2 of VRN1 may similarly serve as a linker region of no great importance to VRN1 function. Alternatively, region 2 may function as a novel type of transcriptional activation or repression domain, or in some other, unknown, function of VRN1. Table 4 gives information on the sequences which were used in comparisons with VRN1. The RTV1 gene is discussed below.

(B) Effect of the Allelic Mutations on VRN1

The mutations found in the two mutant alleles of vrn1 (FIG. 6) and the effect of these mutations on the resulting encoded protein can be correlated with the phenotypic severity, i.e., effect on vernalization response (FIG. 1A), of the two alleles. As shown in FIG. 7, the vrn1-1 allele encodes a polypeptide of only 47 aa, and the vrn1-2 allele encodes a polypeptide of 194 aa (the last six of which are incorrect due to a frameshift) compared to 341 aa for the wild-type protein. The fact that the polypeptide encoded by vrn1-2 contains the first B3 domain as well as the putative PEST regions and NLS but is only slightly less severe in its effect on vernalization than the vrn1-1 allele (FIG. 1A), suggests that the second B3 DNA-binding domain may be required (but not necessarily sufficient) for VRN1 function under the conditions used.

(C) The RTV1 Gene, a Relative of VRN1

Despite the presence of many plant proteins that contain the B3 domain, only one putative protein sequence has been found with a domain structure identical to VRN1, i.e., containing regions 1–3 in the same configuration and with no additional domains. The gene encoding this protein, which is represented in the *Arabidopsis* EST database (Table 4), has been named RTV1 (related to VRN1). RTV1, which is on IGF BAC clone F13F21 on chromosome 1, encodes a protein of 301 aa which is very similar to VRN1 (Table 5). While the overall similarity between RTV1 and VRN1 is 74% (within the coding region), the similarity is greatest at the C-terminal end, with region 3 of RTV1 and VRN1 being 99% similar (Table 5). Outside of the coding region (i.e., in the UTRs, promoter region and introns), the VRN1 and RTV1 genes appear to be unrelated. However, the intron/exon organization of the RTV1 gene is similar to VRN1 and therefore the two genes are likely to be the result of a duplication event. The most notable difference between VRN1 and RTV1 is the deletion of 33 amino acids in the first B3 domain of RTV1. It is worth noting that this deletion does not affect the C-terminal, most conserved, portion of the B3 domain.

The finding of a gene that is very closely related to VRN1 suggests that RTV1 may serve a function in vernalization response or other aspect of flowering time control. Since the vrn1-1 allele encodes a short polypeptide of only 47 amino acids, with no complete putative DNA-binding domain (FIG. 7) it is likely to encode a non-functional polypeptide. The fact that vrn1-1 mutant plants still retain a small response to vernalization (FIG. 1) suggests the presence of other *Arabidopsis* factors that can partially substitute for VRN1 function. Since RTV1 is a closely-related VRN1 paralogue in *Arabidopsis* it may be such a factor.

Another factor that may possibly be responsible for this functional redundancy is VRN2 (Chandler et al., 1996). Like vrn1-1 fca-1 mutants, vrn2-1 fca-1 mutants also retain a partial response to vernalization, but vrn1-1 vrn2-1 fca-1 triple mutants do not (data not shown). If it is assumed that vrn1-1 is a "null" mutation, then this result suggests that VRN1 and VRN2 act in separate and partially redundant vernalization-promoting pathways.

Example 9

Detection and Isolation of VRN1-Related Genes From other Plant Species

A high-stringency Southern blot of genomic DNA from various cereals, when hybridized with a probe corresponding to the VRN1 transcript, specifically detected VRN1-related genes in millet (FINGER, FOXTAIL 863B-PEARL, 841B-PEARL), sorghum (p20, P10), barley (BETZER, TRIUMPH, IGRI), rice (63–83, IR20), wheat (SYNTHETIC, SQ1, CHINESE SPRING), and maize (P9, P10, C0, C8, C2, C9, DPT A, DTP79, B73, M017, B84, 12B84, L175, L25, DTP A, DW) (results not shown).

To prepare the blot, approximately 10 μg of genomic DNA from each of these varieties was digested with Eco RI (37° C., overnight). DNA samples were separated by gel electrophoresis on a 0.8% agarose gel run at 50V for 16 hours. The gel was then processed for Southern blotting by standard procedures (see Maniatis, supra) and DNA was blotted overnight onto a nylon membrane (Hybond-N, Amersham). Following blotting, the DNA was cross-linked to the filter by exposure to UV light according to the manufacturer's recommendations and baked at 80° C. for 2 hrs.

The VRN1 cDNA probe V2V6 was prepared by amplifying an aliquot of the first-strand cDNA synthesis from total RNA of *Arabidopsis* seedlings with the oligonucleotide primers V2 and V6. The resulting PCR product was purified by agarose gel electrophoresis and labeled with $^{32}$P-dCTP by the random hexamer priming method (see Maniatis, supra).

Hybridisation of the filter with the radiolabelled probe, and subsequent washes, were under standard high stringency conditions using buffer comprising 5×SSC, 5× Denhart's solution, and 0.5% SDS at 65° C. for 16 hours. The filter was then washed sequentially in (1) 2×SSC, 0.1% SDS at room temperature for 10 minutes; (2) 1×SSC, 0.1% SDS at 65° C. for 15 minutes; and (3) 0.1×SSC, 0.1% SDS at 65° C. for 10 minutes.

The washed filter was exposed to a PhosphorImager plate (Molecular Dynamics) for 3 days prior to visualisation.

In the light of the results above, in addition to the monocots, it is highly probable that VRN1-related genes will be found to exist in agronomically important dicot species (e.g. Brassicaceae, sugarbeet, peas and celery etc.)

Thus the provision of sequence information for the VRN1 gene of *Arabidopsis thaliana* enables the obtention of homologous sequences from cDNA or genomic libraries from other plant species, such as can be prepared or obtained by the skilled person without undue burden. Positive clones can be further analyzed by restriction endonuclease digestion and Southern blotting as described hereinbefore. Particularly preferred are homologues from commercially important species that have a vernalization requirement, or show some response to vernalization.

Materials and Methods used in Examples

Plant growth

For vernalization treatments, seeds were sown on fine grit (Levington's M3) in individual pots, and germinated for increasing durations at 4° C., 8 hr light:16 hr dark, 5 mmol m$^{-2}$ sec$^{-1}$ light intensity. For dose-response experiments seed sowing was staggered, with all plants removed from the vernalization conditions simultaneously. Following vernalization, seedlings were placed into a controlled environment chamber (Gallenkamp), 20° C., 16 hr light: 8 hr dark 90 mmol m$^{-2}$ sec$^{-1}$ light intensity. Seedlings receiving no vernalization treatment were stratified for 2 days under vernalization conditions, and grown for two days prior to transfer in to the growth cabinet. Plants were grown for 10 days, and then pricked out into individual compartments of P40 trays. Flowering time was measured by counting total leaf number (i.e. rosette and cauline leaves) by marking the leaves with permanent black ink as they emerged.

Genetic Mapping

VRN1 was initially positioned on Chromosome 3 through linkage to RFLP markers mi339 and mi207 (Liu et al., 1996), in F2 progeny (154 chromosomes) of a cross between vrn1-1 fca-1 (Ler background) and fca-10 (Ws background), as described in (Chandler et al., 1996). As a first step in refining this map position, two existing RLFP markers in the region (g4711 and m560B2; Chang et al., 1988), and two existing SSLP markers in the region (ATHCHIB and ngal62; Bell and Ecker, 1994), were scored on a larger F2 population (988 chromosomes) of the same cross as above. In order to refine the map position of VRN1 further, new genetic markers that were polymorphic between Ler and Ws were developed (Table 1). Standard techniques (e.g., restriction digestion, $^{32}$P-labeling of probes, agarose gel electrophoresis, Southern blotting, and PhosphorImager detection) were used throughout.

Physical Mapping

YAC, BAC and cosmid clones and libraries were handled, analyzed, and hybridized according to standard procedures (Schmidt and Dean, 1995; Bent et al., 1998; Macknight et al., 1997). As with the genetic mapping of VRN1, some probes and PCR markers were existing and available, and some were developed in order to establish or refine the overlap between clones. The following probes and PCR markers were existing and available: mi289, GBGe303, MSH2, ve039, mi339, agp14, MAP2K, sAT2105b, and m506B2. New probes and PCR markers developed in order to identify the VRN1 gene are listed in Table 2. New probes and PCR markers were developed by three methods: (1) iPCR of BAC ends, (2) design of PCR primers based on BAC end sequence data (from TIGR;website address:www.tigr.org/tdb/at/atgenome/bac_end_search/bac_end_search.html), and (3) sequencing of cosmid ends and design of PCR primers based on the obtained data.

(A) iPCR of pBelo-BAC Ends

The following procedure is a modification of a protocol received from T. Altmann (MPI, Golm, Germany). DNA from ⅒oth of a 25 ml BAC overnight culture was digested with (1) HhaI or EcoRI or HincII or RsaI for the T7 end, or (2) HhaI or HaeII or EcoRV for the Sp6 end, and phenol chloroform extracted and ethanol precipitated. Digested material was ligated in a 100 μl standard reaction with T4 DNA ligase, heat inactivated, and ethanol precipitated. Ligation products were digested with PvuI for the T7 end, and BsrBI for the Sp6 end in a 15 μl reaction volume. For PCR, 1 μl of digestion reaction was amplified in a standard reaction using (1) primers BACT7U and BACT7L for the T7 end, or (2) primers Sp6A and Sp6B for the Sp6 end.

| | | | |
|---|---|---|---|
| BACT7U | 5'- CCTCTTCGCTATTACGCCAG -3' | (SEQ ID NO: 16) |
| BACT7L | 5'- GCCCTTCCCAACAGTTCG -3' | (SEQ ID NO: 17) |
| Sp6A | 5'- CACACAGGAAACAGCTAT -3' | (SEQ ID NO: 18) |
| Sp6B | 5'- ACACAACATACGAGCCGGAA -3' | (SEQ ID NO: 19) |

(B) Sequencing of Cosmid DNA and PCR Products

Genomic sequence was obtained from the ends of cosmid insert DNA using the BIGDYE cycle sequencing kit (Perkin Elmer Applied Biosystems), and T3 and T7 primers, whose sequences flank the genomic DNA insert site. For sequencing regions further into the cosmid insert DNA, and for sequencing PCR products amplified off of genomic DNA from the vrn1-1 and vrn1-2 alleles, the oligonucleotides shown in Table 3 were used. The reactions were run on an ABI377 machine, and compiled using the SeqMan (DNAStar, Lasergene) program.

Cosmid Complementation

Cosmids in the 04541 binary vector were mobilized into *Agrobacterium tumefaciens* (strain C58C1 Rif$^R$) by tri-parental mating (Hoekema et al., 1983). vrn1-1 fca-1 plants were transformed with these *Agrobacterium* strains by root infection (Hooykaas, 1989). Transgenic plants were selected on GM with Kanamycin (50 mg/mL), and transferred to soil when they had reached the 3–4 leaf stage. The presence of each cosmid in the transgenic lines was confirmed using a specific diagnostic PCR reaction, using a primer present within the cosmid insert sequence and a primer present in the cosmid flanking the insert site. T2 seed were collected, and analyzed for the segregation of Kanamycin resistance or sensitivity on GM plates containing Kanamycin (as above), scored 14–20 days after germination. Lines that segregated a 3:1 ratio of resistant to sensitive plants were tested for their ability to complement the vrn1-1 mutant phenotype, by vernalizing for 5 weeks and recording the total leaf number.

RT-PCR and 3'-RACE

In order to determine the intron-exon structure of the VRN1 gene, RT-PCR reactions using total RNA prepared from fca-1 and vrn1-1 fca-1 seedlings grown on soil were performed according to standard procedures (Frohman et al., 1988). The PCR products were sequenced using both the primers used for PCR, and selected internal primers, using the BIGDYE kit (PE Applied Biosystems). The reactions were run on an ABI377 machine, and compiled using the SeqMan (DNAStar, Lasergene) program.

Sequence Comparisons

The nucleic acid sequence comparison in Table 5 was by using the Jotun Hein method (weighted residue table) of MegAlign (DNAstar). Genomic and cDNA sequences were aligned using the BLAST 2 SEQUENCES program (website address: www.ncbi.nlm.nih.gov/gorf/b12.html) from NCBI.

Parameters are preferably set, using the defaults, as follows:

Gap penalty: 11

Gap length penalty: 3

KTUP word length: 6

Amino acid sequences were initially aligned using the Clustal method, using the PAM 250 residue weight table, and further adjusted manually. For amino acid similarity comparisons, amino acids were-grouped into five classes on the basis of physiochemical properties, as follows: (1) hydrophobic—G, A, V, P, M, I, L; (2) polar—S, T, N, Q, C; (3) bulky ring—Y F, W, H; (4) positively charged—K, R; (5) negatively charged —D, E.

TABLE 1

Genetic markers developed in order to identify the VRN1 gene.

| Marker | Type | Ler/Ws polymorphism |
|---|---|---|
| GBGe303 | RFLP | SspI; Ler band < Ws band |
| MSH2 | CAPS | Sau3A; Ler: 2 sites, Ws: no sites |
|  |  | EfaI; Ler: no sites, Ws: 1 site |
| ve039 | CAPS | RsaI; Ler: 3 sites, Ws: 2 sites |
| agp14 | RFLP | HpaII; Ler band < Ws band |
| pKS1240 | RFLP | DraI; Ler band > Ws band |
| MAP2K | RFLP | HaeIII; Ler band < Ws band |

TABLE 2

Physical mapping markers developed in order to identify the VRN1 gene.

| Marker | Type | Method used to develope |
|---|---|---|
| T4L24-T7 | Southern probe | iPCR |
| T7H5-SpG | Southern probe | iPCR |
| T15C16-Sp6 | Southern probe | iPCR |
| T10N5-T7 | Southern probe | iPCR |
| T24F13-T7 | PCR diagnostic | BAC end sequence data (public) |
| 8H8-T7 | PCR diagnostic | cosmid end sequence (obtained) |
| F25C7-T7 | PCR diagnostic | BAC end sequence data (public) |
| 10F10-T3 | PCR diagnostic | cosmid end sequence (obtained) |
| 8H8-T3 | PCR diagnostic | cosmid end sequence (obtained) |
| F18G1-T7 | PCR diagnostic | BAC end sequence data (public) |
| 10F10-T7 | PCR diagnostic | cosmid end sequence (obtained) |
| T4L24-Sp6 | PCR diagnostic | BAC end sequence data (public) |
| T20A21-Sp6 | Southern probe | iPCR |
| T7H5-T7 | Southern probe | iPCR |
| T15C16-T7 | Southern probe | iPCR |
| F10N5-Sp6 | Southern probe | iPCR |
| T24F13-Sp6 | Southern probe | iPCR |
| F28N8-Sp6 | PCR diagnostic | BAC end sequence data (public) |
| F5G10-T7 | PCR diagnostic | BAC end sequence data (public) |

TABLE 3

Oligonucleotides developed to identify the VRN1 gene. The positive (+) strand oligos correspond to the forward, or mRNA, strand of DNA, and the negative (−) strand oligos correspond to the reverse, or coding, strand of DNA. The position indicated in the table refers to the nucleotide position in the VRN1 genomic sequence (Annex I) of the 5' end of the oligo.

| Oligo | Strand | Position | Sequence (5' to 3') | |
|---|---|---|---|---|
| S63 | + | 850 | CAACGGTTAGCCCAAAC | (SEQ ID NO: 20) |
| S64 | − | 866 | GTTTGGGCTAACCGTTG | (SEQ ID NO: 21) |
| V11 | + | 1193 | GAGACCAGTTTTGTTTTCC | (SEQ ID NO: 22) |
| S62 | − | 1229 | GACAAATATAGGTGGAAAGG | (SEQ ID NO: 23) |
| S66 | + | 1441 | AAAGGGGAGTAGGTGGG | (SEQ ID NO: 24) |
| V7 | + | 1811 | CTCTCTGGTCTTCTCTTC | (SEQ ID NO: 25) |
| V10 | − | 1828 | GAAGAGAAGACCAGAGAG | (SEQ ID NO: 26) |
| V6 | + | 1907 | TTTTCTCATCCACTATCC | (SEQ ID NO: 27) |
| S51 | − | 1930 | TTTCTTGGATAGTGGATGAG | (SEQ ID NO: 28) |
| S65 | − | 2166 | AAAACAGGGAAGAGTAAGAAG | (SEQ ID NO: 29) |
| S52 | + | 2270 | CATTGGTTGTGTTTGGTGGG | (SEQ ID NO: 30) |
| V5 | + | 2599 | GGTCTCTATGTATTGTGC | (SEQ ID NO: 31) |
| V4 | − | 2616 | GCACAATACATAGAGACC | (SEQ ID NO: 32) |
| V12 | − | 2846 | AGATTGATTACACGACTCC | (SEQ ID NO: 33) |
| V8 | + | 3125 | CCCAGATAAGTTTGTGAG | (SEQ ID NO: 34) |
| V3 | + | 3391 | ATTCCGCTCACAACCAC | (SEQ ID NO: 35) |
| V15 | − | 3414 | GTTTGAAGTGGTTGTGAG | (SEQ ID NO: 36) |
| V14 | + | 3477 | TACCCATCACCACTTCC | (SEQ ID NO: 37) |
| S60 | − | 3474 | CAGAAGAAGGAAAGATGACC | (SEQ ID NO: 38) |
| S61 | + | 3927 | GAACAAAGAGAGAGAGCC | (SEQ ID NO: 39) |
| V13 | + | 3976 | ACCCTTTCTTCAGAGTG | (SEQ ID NO: 40) |
| V9 | − | 3942 | CTCTCTCTCTTTCTTCTG | (SEQ ID NO: 41) |
| V16 | − | 3993 | CCACTCTGAAGAAAGGG | (SEQ ID NO: 42) |
| S46 | + | 4096 | CCTTCTGTTTCTGTTTCTC | (SEQ ID NO: 43) |
| S45 | − | 4114 | GAGAAACAGAAACAGAAGG | (SEQ ID NO: 44) |
| V2 | − | 4431 | AAGATACTCCTACACGAC | (SEQ ID NO: 45) |
| V17 | + | 4486 | GTCTCGTTTTTTCTCTCGG | (SEQ ID NO: 46) |
| S49 | − | 4870 | CTACCACAGTTCCCACCTAC | (SEQ ID NO: 47) |

TABLE 4

Sequences corresponding to ESTs for VRN1 and RTV1, and other sequences used for comparison to VRN1.

| Name | Type | Description | Accession # |
|---|---|---|---|
| 92M2 | nucl. | EST; VRN1 transcript | T21005 |
| F2H7 | nucl. | EST; VRN1 transcript | N95889 |
| 105O22 | nucl. | EST; RTV1 transcript | T22671 |
| 151H18 | nucl. | EST; RTV1 transcript | T76788 |
| 247A13 | nucl. | EST; RTV1 transcript | AA713228 |
| 89H14 | nucl. | EST; RTV1 transcript | T20909 |
| 89I23 | nucl. | EST; RTV1 transcript | T20917 |
| VRN1 | aa | Encoded by VRN1 (putative) | N/A |
| RTV1 | aa | Encoded by RTV1 (putative) | N/A |
| 3859591 | aa | Putative *Arabidopsis* protein | AAC72857 |
| CAA19759 | aa | Putative *Arabidopsis* protein | CAA19759 |
| CAA19755 | aa | Putative *Arabidopsis* protein | CAA19755 |
| CAA19754 | aa | Putative *Arabidopsis* protein | CAA19754 |
| RAV1 | aa | Putative *Arabidopsis* protein | BAA34250 |
| FUSCA3 | aa | Putative *Arabidopsis* protein | AAC35246 |
| ABI3 | aa | Putative *Arabidopsis* protein | JQ1676 |
| ARF1 | aa | Putative *Arabidopsis* protein | AAD39318 |
| IAA24 | aa | Putative *Arabidopsis* protein | AAB92476 |
| c-MYC | aa | Putative *Carassius auratus* (goldfish) protein | P49709 |

TABLE 5

Comparison of the Nucelotide and Amino Acid Sequences of RTV1 to VRN1

| Sequence | Nucleotides | | | Amino Acids | | | |
|---|---|---|---|---|---|---|---|
| | Id[a] | Length (bp) | Range[b] | Id[a] | Sim.[c] | Length (aa) | Range[d] |
| RTV1 complete | 69 | 1026 | 269–1291 | 67 | 74 | 341 | 1–341 |
| RTV1 Region 1 | 49 | 283 | 272–550 | 42 | 44 | 93 | 2–94 |
| RTV1 Region 2 | 71 | 429 | 551–981 | 71 | 82 | 144 | 95–238 |
| RTV1 Region 3 | 84 | 314 | 982–1291 | 95 | 99 | 103 | 239–341 |

[a]Identity (%)
[b]Numbered relative to VRN1 transcript sequence (FIG. 7)
[c]Similarity (%)
[d]Numbered relative to VRN1 encoded amino acid sequence (FIG. 7)

REFERENCES

Abe, H., Yamaguchi-Shinozaki, K., Urao, T., Iwasaki, T., Hosokawa, D., and Shinozaki, K. (1997). Role of *arabidopsis* MYC and MYB homologs in drought- and abscisic acid- regulated gene expression. Plant Cell 9, 1859–68.

Abel, S., Oeller, P. W., and Theologis, A. (1994). Early auxin-induced genes encode short-lived nuclear proteins. Proc Natl Acad Sci USA 91, 326–30.

Baker, S. S., Wilhelm, K. S., and Thomashow, M. F. (1994). The 5'-region of *Arabidopsis thaliana* cor15a has cis-acting elements that confer cold-, drought- and ABA-regulated gene expression. Plant Mol Biol 24, 701–13.

Barnes, J. A., and Gomes, A. V. (1995). PEST sequences in calmodulin-binding proteins. Mol Cell Biochem 149–150, 17–27.

Becker, D., Brettschneider, R., and Lorz, H. (1994). Fertile transgenic wheat from microprojectile bombardment of scutellar tissue. Plant J 5, 299–307.

Bell, C. J., and Ecker, J. R. (1994). Assignment of 30 Microsatellite Loci to the Linkage Map of *Arabidopsis*. Genomics 19, 137–144.

Bent, E., Johnson, S., and Bancroft, I. (1998). BAC representation of two low-copy regions of the genome of *Arabidopsis thaliana*. Plant J 13, 849–55.

Camilleri, C., Lafleuriel, J., Macadre, C., Varoquaux, F., Parmentier, Y., Picard, G., Caboche, M., and Bouchez, D. (1998). A YAC contig map of *Arabidopsis thaliana* chromosome 3. Plant J 14, 633–42.

Chandler, J., Wilson, A., and Dean, C. (1996). *Arabidopsis* mutants showing an altered response to vernalization. Plant Journal 10, 637–644.

Chang, C., Bowman, J. L., DeJohn, A. W., Lander, E. S., and Meyerowitz, E. M. (1988). Restriction fragment length polymorphism linkage map for *Arabidopsis thaliana*. Proc Natl Acad Sci USA 85, 6856–60.

Chevaillier, P. (1993). Pest sequences in nuclear proteins. Int J Biochem 25, 479–82.

Classon, M., Wennborg, A., Henriksson, M., and Klein, G. (1993). Analysis of c-Myc domains involved in stimulating SV40 replication. Gene 133, 153–61.

Cooper, K. F., Mallory, M. J., Smith, J. B., and Strich, R. (1997). Stress and developmental regulation of the yeast C-type cyclin Ume3p (Srb11p/Ssn8p). Embo J 16, 4665–75.

Frohman, M. A., Dush, M. K., and Martin, G. R. (1988). Rapid production of full-length cDNAs from rare transcripts: amplification using a single gene-specific oligonucleotide primer. Proc Natl Acad Sci USA 85, 8998–9002.

Gilmour, S. J., and Thomashow, M. F. (1991). Cold-acclimation and cold-regulated gene-expression in ABA mutants of *Arabidopsis thaliana*. Plant Molecular Biology 17, 1233–1240.

Giraudat, J., Hauge, B. M., Valon, C., Smalle, J., Parcy, F., and Goodman, H. M. (1992). Isolation of the *Arabidopsis thaliana* ABI3 (Abscisic acid-insensitive) gene by positional cloning. The Plant Cell 4, 1251–1261.

Goldsbrough, A. P., Albrecht, H., and Stratford, R. (1993). Salicylic acid-inducible binding of a tobacco nuclear protein to a 10 bp sequence which is highly conserved amongst stress-inducible genes. Plant J 3, 563–71.

Gomes, A. V., and Barnes, J. A. (1997). Protein phosphatases are pest containing proteins. Biochem Mol Biol Int 41, 65–73.

Guilfoyle, T. J., Ulmasov, T., and Hagen, G. (1998). The ARF family of transcription factors and their role in plant hormone- responsive transcription. Cell Mol Life Sci 54, 619–27.

Hoekema, A., Hirsch, P. R., Hooykaas, P. J. J., and Schilperoort, R. A. (1983). A binary plant vector strategy based on separation of vir- and T-region of the *Agrobacterium tumefaciens* Ti-plasmid. Nature 303, 179–180.

Hooykaas, P. J. (1989). Transformation of plant cells via *Agrobacterium*. Plant Mol Biol 13, 327–36.

Jiang, C., Iu, B., and Singh, J. (1996). Requirement of a CCGAC cis-acting element for cold induction of the BN115 gene from winter *Brassica napus*. Plant Mol Biol 30, 679–84.

Kagaya, Y., Ohmiya, K., and Hattori, T. (1999). RAV1, a novel DNA-binding protein, binds to bipartite recognition sequence through two distinct DNA-binding domains uniquely found in higher plants. Nucleic Acids Res 27, 470–8.

Kerkhoff, E., and Bister, K. (1991). Myc protein structure: localization of DNA-binding and protein dimerization domains. Oncogene 6, 93–102.

Kim, J., Harter, K., and Theologis, A. (1997). Protein—protein interactions among the Aux/IAA proteins. Proc Natl Acad Sci USA 94, 11786–91.

Koepp, D. M., Harper, J. W., and Elledge, S. J. (1999). How the cyclin became a cyclin: regulated proteolysis in the cell cycle. Cell 97, 431–4.

Laney, J. D., and Hochstrasser, M. (1999). Substrate targeting in the ubiquitin system. Cell 97, 427–30.

Liu, Y. G., Mitsukawa, N., Lister, C., Dean, C., and Whittier, R. F. (1996). Isolation and mapping of a new set of 129 RFLP markers in *Arabidopsis thaliana* using recombinant inbred lines. Plant J 10, 733–6.

Liu, Z. P., Galindo, R. L., and Wasserman, S. A. (1997). A role for CKII phosphorylation of the cactus PEST domain in dorsoventral patterning of the *Drosophila* embryo. Genes Dev 11, 3413–22.

Loake, G. J., Faktor, O., Lamb, C. J., and Dixon, R. A. (1992). Combination of H-box [CCTACC(N)7CT] and G-box (CACGTG) cis elements is necessary for feedforward stimulation of a chalcone synthase promoter by the phenylpropanoid-pathway intermediate p-coumaric acid. Proc Natl Acad Sci USA 89, 9230–4.

Luerssen, H., Kirik, V., Herrmann, P., and Misera, S. (1998). FUSCA3 encodes a protein with a conserved VP1/AB13- like B3 domain which is of functional importance for the regulation of seed maturation in *Arabidopsis thaliana*. Plant J 15, 755–64.

Macknight, R., Bancroft, I., Page, T., Lister, C., Schmidt, R., Love, K., Westphal, L., Murphy, G., Sherson, S., Cobbett, C., and Dean, C. (1997). FCA, a gene controlling flowering time in *Arabidopsis*, encodes a protein containing RNA-binding domains. Cell 89, 737–745.

Mannervik, M., Nibu, Y., Zhang, H., and Levine, M. (1999). Transcriptional coregulators in development. Science 284, 606–9.

Marchal, C., Haguenauer-Tsapis, R., and Urban-Grimal, D. (1998). A PEST-like sequence mediates phosphorylation and efficient ubiquitination of yeast uracil permease. Mol Cell Biol 18, 314–21.

Maule, J. (1997). Physical mapping by pulsed-field gel electrophoresis. Methods Mol Biol 68, 93–121.

McCarty, D. R., Hattori, T., Carson, C. B., Vasil, V., Lazar, M., and Vasil, I. K. (1991). The Viviparous-1 developmental gene of maize encodes a novel transcriptional activator. Cell 66, 895–905.

McKinsey, T. A., Chu, Z. L., and Ballard, D. W. (1997). Phosphorylation of the PEST domain of IkappaBbeta regulates the function of NF-kappaB/IkappaBbeta complexes. J Biol Chem 272, 22377–80.

Mhiri, C., Morel, J. B., Vernhettes, S., Casacuberta, J. M., Lucas, H., and Grandbastien, M. A. (1997). The promoter of the tobacco Tnt1 retrotransposon is induced by wounding and by abiotic stress. Plant Mol Biol 33, 257–66.

Mozo, T., Fischer, S., Shizuya, H., and Altmann, T. (1998). Construction and characterization of the IGF *Arabidopsis* BAC library. Mol Gen Genet 258, 562–70.

Nordin, K., Vahala, T., and Palva, E. T. (1993). Differential expression of two related, low-temperature-induced genes in *Arabidopsis thaliana* (L.) Heynh. Plant Mol Biol 21, 641–53.

Rechsteiner, M., and Rogers, S. W. (1996). PEST sequences and regulation by proteolysis. Trends Biochem Sci 21, 267–71.

Rogers, S., Wells, R., and Rechsteiner, M. (1986). Amino acid sequences common to rapidly degraded proteins: the PEST hypothesis. Science 234, 364–8.

Schmidt, E. V. (1999). The role of c-myc in cellular growth control. Oncogene 18, 2988–96.

Schmidt, R., and Dean, C. (1995). Hybridization analysis of YAC clones. Methods in Mol.& Cell.Biol. 5, 309–318.

Steger, D. J., Utley, R. T., Grant, P. A., John, S., Eberharter, A., Cote, J., Owen-Hughes, T., Ikeda, K., and Workman, J. L. (1998). Regulation of transcription by multisubunit complexes that alter nucleosome structure. Cold Spring Harb Symp Quant Biol 63, 483–91.

Stockinger, E. J., Gilmour, S. J., and Thomashow, M. F. (1997). *Arabidopsis thaliana* CBF1 encodes an AP2 domain-containing transcriptional activator that binds to the C-repeat/DRE, a cis-acting DNA regulatory element that stimulates transcription in response to low temperature and water deficit. Proc Natl Acad Sci USA 94, 1035–40.

Stone, J., de Lange, T., Ramsay, G., Jakobovits, E., Bishop, J. M., Varmus, H., and Lee, W. (1987). Definition of regions in human c-myc that are involved in transformation and nuclear localization. Mol Cell Biol 7, 1697–709.

Suzuki, M., Kao, C. Y., and McCarty, D. R. (1997). The conserved B3 domain of VIVIPAROUS1 has a cooperative DNA binding activity. Plant Cell 9, 799–807.

Thomashow, M. F. (1994). *Arabidopsis thaliana* as a model for studying mechanisms of plant cold tolerance. In *Arabidopsis* (New York: Cold Spring Harbor Laboratory Press), pp. 807–834.

Torchia, J., Glass, C., and Rosenfeld, M. G. (1998). Co-activators and co-repressors in the integration of transcriptional responses. Curr Opin Cell Biol 10, 373–83.

Ulmasov, T., Hagen, G., and Guilfoyle, T. J. (1997). ARF1, a transcription factor that binds to auxin response elements. Science 276, 1865–8.

Urao, T., Yamaguchi-Shinozaki, K., Urao, S., and Shinozaki, K. (1993). An *Arabidopsis* myb homolog is induced by dehydration stress and its gene product binds to the conserved MYB recognition sequence. Plant Cell 5, 1529–39.

Vierstra, R. D. (1996). Proteolysis in plants: mechanisms and functions. Plant Mol Biol 32, 275–302.

Yaglom, J. A., Goldberg, A. L., Finley, D., and Sherman, M. Y. (1996). The molecular chaperone Ydj1 is required for the p34CDC28-dependent phosphorylation of the cyclin Cln3 that signals its degradation. Mol Cell Biol 16, 3679–84.

```
    Annex I-Ler VRN1 genomic
       (contig 29 [1501-6500])

1        10        20        30        40
TTTAAAATTCGAATTGGGATTTAAGAAAAATTCTCATCAA

ATATTTATCATTAGTGTATATATATCAGTGTTTTACATTT

GTTAATCCTAAATAATAAACCGATCTGAAAAGTTGATAAA

TGCGTTGTCAAAAGACAAAATATACATCCAAACAAATCAC

GTGATTGCCTTCAACTTGCCACgGGTTCAAAGATTTAACA

AATCTTCTAAAACACCAACTTAACCCACGAATACACAAGC

ACAGAGTGGTGGTAAACATACAAGTTAATGAGTTATTCAA

ATGAGATTTTCAATATCATTCTTCTTCAGCCCGTCACAAG

AAGCCAAGATTAAGCCATTAGAGGAAGTTTATAAACCGAC

AAAACCTGCTTAGATACAAAGAATACTAGCTAATGTGTTT

CAACAAACTTCAAATTGACGATACGTTACATTCATATTAA

TCACTTCAGAGCTTGATTATTCAAATTATTTTTTCTACTG

TGATACATATATACACACATGTTTTGCTTTTCTATGATTC

TATCTACATTTTCATACCGTTGAATAATTTATGTATGAAT

TACGATGCAATTTCCTTCATTATGCTTGAATAAAATGCTT

TTGGACATGCATGCGATATTGGATCTACTTTTGGATTCTA

TTTTTAAAAATCAGCGAGTTTGTTGCTTTGTAATTTTTAA

TTAGGCATCAAGAATTTCTAAAATGCACGCGAACTGGTGA

AAAGAGGAATGTTTACGTTTACCCCTTTATTTTCTTACAG

CTCATAAGGATACTGTCAGAAGACAGAACCAAGGCTCTCT

GACTATAAATTGGAATCCATTTAAACATAATGTTATGACC

AATGATGGCCAACGGTTAGCCCAAACTAATTAACTACAAG

TCAAGTTCCAATATTCTAAGGAGAAATAATAGTATACTAA

ACATACATTAGAGAGGTTAAACTTCTTTTTGGATTTAAGT
```

Annex I—Ler VRN1 genomic (contig 29 [1501–6500])

```
GTGTATGCATAGGCTATTTATTCTTAAGTATAACTATTAA
CTGTAGCTAGATTTATACAAGAAATACATAAAACTTTATG
CATGTGAGGTAGCCATGAATATACGTACATGTTGCAATCG
ATTATACATGTTGTATTTGGATTTCTCTATACATGTTTTA
ACTTGTCATTCTCTAAGTATATACATACCATTAATACTGT
GGGCATGAGTTTATGATAAGACTTTTCTTTTGGAGACCAG
TTTTGTTTTCCTTTCCACCTATATTTGTCTATAGGCTTCa
gACGGTACACTAGTTTACAAGTGTTTTTATATGTTCTAAA
TAAAATTGAGATTTTCCGGAACGGTATGATCTGTTTGCAA
ATAAGGACGTATATATAACAGTATCAAATATATTTGTTGT
TATAAGGCAATAATATATTTTCTGAGATATTGCGTGTTAC
AAAAAAGAAATATTTGTTAAGAAAAAAAAAGATGGTCGAA
AAAGGGGAGTAGGTGGGGCGGTCGGCTTTTGATTAGTTA
ATAAAAGAAACCACACGAGTGACCTACCGATTCGACTCAA
CGAGTCTACCGAGCTAACACAGATTCAACTCGCTCGAGCT
TCGTTTTATGACAAGTTGGTTTTTTTTTTTTTTTTTAAT
TTTTTCATCTTCTTGGGTTTGGTTGGGTCACTCTTCAGGT
CAGGTGTGTAAAAAAGAAAGAAAGAAAAGAGAGATTGTTG
TGTTGTAACCCCTTTGACTAAAATCTAATGAACTTTTTTA
ACACAACAAAACTCCTTCAGATCTGAAAGGGTTCTTCTTC
TCTCTTAGTCTCTTTGTCCTTTTATTCTCCGTCGTCGTTT
CATGATCTGACTCTCTGGTCTTCTCTTCTTCTTCTTCTTC
TTCTATTTTTCTTACTTCGTCACTGTTGTGTCTGAACAT
GCCACGCCCTTCTTCCATAAGTTGATTTTCTCATCCACT
ATCCAAGAAAAACGTCTGGTAACTTACTCTCTCTCTCT
CTCTCTCTCTGTTCTCCTTCTCCTCATCTTTCAAAGTTTT
GATTTTGTGCGAAATTGAGGGTTTTCAAGGTTTGGAATCT
GGTGAACGAGTTTGTAAGATTATGCCTTGTGACACTCTTG
CTTGATTTCTTACAATTCACTTGTATTGATTCTTTGTAAG
AATCGAGTCAAGGTTGTGCTTTTATCTTCTTACTCTTCCC
TGTTTTGGGTAATGAAAAGAAGTTCCATTTTTGAACTTTG
TGTTGTCTTATTGGTCAAATGAGAATTTGTGGGTTTCCAA
TGGAAGTCTGCAAGACAGTTTCTTTTGGTCATTGGTTGTG
TTTGGTGGGAAATTGGGTATTTGATGGTATATCTGTACTC
TGACAGCATATTGTGTGTAGTTTGGGAATTTTTTTTTTTT
TTTTGAGTGATTTGACTTTTGGAGGACGATTTGATTCTGT
CAGATTGATCAAATTTCTTCTGAGGAGAAAAAGTTGAGAT
CTGTTTATGGTTTCTCTATTATAAATGTCTGTTTTGTTTA
CTCTATTTTGACTGTTTTCTCTGTTTGACTTAGGAATGTC
TGAGATCTTAGACTCCTTATTGAGTATTGTtGGCTTGTG
AGTGAATCCCTAAAACTGAGTAGTTGACTTGTTTTGAAGG
TCTCTATGTATTGTGCTTATGTTTTAAAGTTGTCTACTTT
ATTTGATACAGTGATTAGTCATCACTTGTACAGATTCCCC
CAAGAGCATTGTTTTGAACAAATCCAAATTTGCTTAGCTC
TCCATTTGGCATTTAAGTGACTAGATTTTCTCTGGAATAA
TGATTTCGATTAACACAGGCATTTATGTGGAACCAAGTTT
GCAAATTATTAATGTGATAAGATCATAGGAGTCGTGTAAT
CAATCTATTCAGAGATAAATGTACCATTTTACATGTGTAC
TAATGGACTGTGTCTCCTTGTTGATGCCTTCTCTAAACTG
AAATATGGCCTTTTGGTTTGTGTTTTTAAATTAGGTAAAG
CCGTCGTTTCTTCAGCTACTGTGTTTATTGGATGTTTTTG
CTGAAAAATGTCTGTTTCGATTTGATGTTCTCGCAATATT
CTGTGCTGTTCTTATAGATATTGTGGACATTTATATCATT
ATATGCTTCTTTATATCTCATACCGGCATGCTTGTGCAGA
GGGTCCCAGATAAGTTTGTGAGTAAATTCAAGGATGAGCT
TTCGGTTGCTGTTGCACTCACAGTACCTGATGGTCATGTT
TGRCGTGTAGGACTAAGGAAAGCTGACAACAAAATTTGGT
TTCAAGATGGTTGGCAAGAGTTTGTTGACCGTTACTCCAT
TCGCATTGGTTATCTTTTGATTTTTAGATATGAAGGAAAC
TCTGCCTTCAGCGTCTACATTTTCAATTTATCCCACTCTG
AGATCAATTACCATTCCACCGGTCTCATGGATTCCGCTCA
CAACCACTTCAAACGCGCCCGTTTGTTTGAAGACCTTGAA
GATGAAGATGCCGAGGTCATCTTTCCTTCTTCTGTGTACC
CATCACCACTTCCTGAGTCTACAGTACCAGCCAACAAAGG
GTATGCTAGTTCAGCCATCCAAACCTTGTTCACTGGACCA
GTTAAAGGTGATATTTATAACCAACTGATTCCCTTTATCT
ATCGCTGATTACGCGTCTTATCATTCTTTTGAGGTTGATG
CTTGATATTTTCCTTATCTCCAGCTGAAGAGCCAACGCCA
ACCCCAAAAATACCTAAAAAGAGAGGGAGGAAGAAGaAAA
ATGCTGATCCTGGTAAGCACTTTTCCTCTTTGAAATGCTT
CAGACTCGTTTTCAGAGGATTCACAGATTCTTCCTCATGA
TACATATATCCTTTTGATATTGTCCTTACAGAGGAAATAA
ACTCATCAGCTCCGCGAGATGATGATCCAGAGAACCGTTC
```

Annex I—Ler VRN1 genomic
(contig 29 [1501–6500])

AAAGTTCTACGAGAGTGCTTCTGCGAGAAAGAGAACCGTG

ACTGCAGAAGAAAGAGAGAGAGCCATCAATGCAGCCAAAA

CGTTCGAACCAACAAACCCTTTCTTCAGAGTGGTTCTGCG

ACCATCCTATCTATACAGAGGTTGCATCATGGTAATAAAA

AAACATCTTAGGAAGACTTAATCTTATCGGTGTCTTCACT

GATCTCTAAAAGAAGCCTTCTGTTTCTGTTTCTCTCAACA

GTATCTTCCTTCTGGGTTTGCTGAGAAGTACCTAAGTGGG

ATCTCCGGGTTCATCAAAGTCCAGCTTGCGGAGAAACAAT

GGCCTGTTCGATGTCTCTACAAAGCCGGGAGAGCCAAATT

CAGTCAAGGATGGTACGAATTCACTCTAGAGAACAACTTA

GGAGAAGGAGACGTCTGTGTGTTTGAGCTGCTCAGAACCA

GAGATTTCGTTTTGAAAGTGACAGCCTTTCGAGTCAACGA

GTACGTCTGAACAAAGCATTATGGTGTGATCATTCTGGAT

TTGCAAGTACAATGTCGTGTAGGAGTATCTTAATTTAAAA

Annex I—Ler VRN1 genomic
(contig 29 [1501–6500])

ACAACTAAAAAACTCTCTTCTGGTCTGTGTCATTATTGCG

TCAGTGTCTCGTTTTTTCTCTCGGGTTTACTTTGTGTTAT

CGATGTGGATAAGTTGTTTTTACCTCATTATATATAACCT

CTTGAGTGGAACTCAAATTGTTTGAGTAGAACAAACAAAG

TTAGGGTTTAAGAAGAAGTCTGTAAATACCTAATCTCCAT

CAAATTTGAGTAGAAAGACAAACTGTTCTGGTGGAATACA

AGGAGGGAACTTGAGATAACAAACTTAAGAATAGCCTTCA

AGCCAACGTCTAGAATTTGATGAAGTTGTTGTTTGATCAC

CTCTGAGATAATTGGAAACCCTCTTCATGCAGTTTGCTTG

AGGATACTGGTGAAAATGGGAGTATTGAAGGAAAATGCAT

ATATAAGATTGTAGGTGGGAACTGTGGTAGCAGACACAAC

ACTTGTTCTCTAGACATATACTGTACCAGACATGTTTTGA

TCATAAAACTTAAAAAAAAGAAAACCGTGTGTAAATCAAG

CAAGGAACAACTACAATATTACAATCTTATTGAGATATCA

The invention claimed is:

1. An isolated VRN1 nucleotide sequence encoding a polypeptide which is capable of specifically altering the vernalization response of a plant into which the nucleic acid is introduced and expressed wherein the VRN1 nucleotide sequence:
   (i) encodes the VRN1 polypeptide of SEQ ID NO: 11, or
   (ii) encodes a variant resistance polypeptide which is a homologous variant of SEQ ID NO: 11 which shares at least 95% identity therewith.

2. A nucleic acid as claimed in claim 1 wherein the VRN1 nucleotide sequence is from nucleotides 269–1295 of SEQ ID NO: 10, or a sequence which is degeneratively equivalent thereto.

3. An isolated nucleic acid which comprises a nucleotide sequence which is the complement of the VRN1 nucleotide sequence of claim 1.

4. A recombinant vector which comprises the nucleic acid of claim 1.

5. A vector as claimed in claim 4 wherein the nucleic acid is operably linked to a promoter for transcription in a host cell, wherein the promoter is optionally an inducible promoter.

6. A vector as claimed in claim 5 which is a plant vector.

7. A method for transforming a plant host cell, which comprises the step of introducing the vector of claim 6 into a host cell, and optionally causing or allowing recombination between the vector and the host cell genome such as to transform the host cell.

8. An isolated host cell containing or transformed with the vector of claim 6.

9. A method for producing a transgenic plant, which method comprises the steps of:

(a) performing a method as claimed in claim 7 wherein the host cell is a plant cell, and (b) regenerating a plant from the transformed plant cell.

10. A transgenic plant which is obtained by the method of claim 9, or which is a clone, or selfed or hybrid progeny or other descendant of said transgenic plant, which in each case includes a heterologous nucleic acid wherein said heterologous nucleic acid is a VRN1 nucleotide sequence encoding a polypeptide which is capable of specifically altering the vernalisation response of plant into which the nucleic acid is introduced and expressed.

11. A plant as claimed in claim 10 which is selected from the group consisting of: rice; maize; wheat; barley; oats; rye; oil seed rape; sugar beet; maize; sunflower; soybean; sorghum; lettuce; endive; cabbage; broccoli; cauliflower; carnations; and geraniums.

12. A part of a propagule from a plant as claimed in claim 10, wherein said propagule or part each comprise said heterologous nucleic acid.

13. A method for influencing or affecting the vernalisation phenotype of a plant, which method comprises the step of causing or allowing expression of a heterologous nucleic acid as claimed in claim 1 within the cells of the plant, following an earlier step of introducing the nucleic acid into a cell of the plant or an ancestor thereof.

14. A method as claimed in claim 13 for modifying the kinetics and/or optimal temperature of the vernalization response such as to alter the phenotype of the plant with respect to any one or more of: geographic range; length of a vernalization period; length of a vegetative growth phase.

15. A method as claimed in claim 13 wherein said influencing comprises reducing the vernalisation requirement of a plant, wherein the heterologous nucleic acid is a VRN1 nucleotide sequence encoding a polypeptide which is capable of specifically altering the vernalisation response of plant into which the nucleic acid is introduced and expressed.

* * * * *

SEQUENCE LISTING

<160> NUMBER OF SEQ ID NOS: 48

<210> SEQ ID NO 1
<211> LENGTH: 5000
<212> TYPE: DNA
<213> ORGANISM: Arabidopsis thaliana

<400> SEQUENCE: 1
tttaaaattc gaattgggat ttaagaaaaa ttctcatcaa atatttatca ttagtgtata      60
tatatcagtg ttttacattt gttaatccta aataataaac cgatctgaaa agttgataaa     120
tgcgttgtca aaagacaaaa tatacatcca acaaatcac gtgattgcct tcaacttgcc      180
acgggttcaa agatttaaca aatcttctaa aacaccaact taacccacga atacacaagc    240
acagagtggt ggtaaacata caagttaatg agttattcaa atgagatttt caatatcatt    300
cttcttcagc ccgtcacaag aagccaagat taagccatta gaggaagttt ataaaccgac    360
aaaacctgct tagatacaaa gaatactagc taatgtgttt caacaaactt caaattgacg    420

```
atacgttaca ttcatattaa tcacttcaga gcttgattat tcaaattatt ttttctactg    480
tgatacatat atacacacat gttttgcttt tctatgattc tatctacatt ttcataccgt    540
tgaataattt atgtatgaat tacgatgcaa tttccttcat tatgcttgaa taaaatgctt    600
ttggacatgc atgcgatatt ggatctactt ttggattcta ttttttaaaaa tcagcgagtt   660 tgttgctttg taattttttaa ttaggcatca agaattccta aaatgcacgc gaactggtga   720
aaagaggaat gtttacgttt acccctttat tttcttacag ctcataagga tactgtcaga   780
agacagaacc aaggctctct gactataaat tggaatccat ttaaacataa tgttatgacc   840
aatgatggcc aacggttagc ccaaactaat taactacaag tcaagttcca atattctaag   900
gagaaataat agtatactaa acatacatta gagaggttaa acttctttt ggatttaagt    960 gtgtatgcat aggctattta ttcttaagta taactattaa ctgtagctag atttatacaa   1020
gaaatacata aaactttatg catgtgaggt agccatgaat atacgtacat gttgcaatcg   1080
attatacatg ttgtatttgg atttctctat acatgtttta acttgtcatt ctctaagtat   1140
atacatacca ttaatactgt gggcatgagt ttatgataag actttctttt tggagaccag   1200
ttttgttttc cttccacct atatttgtct ataggcttca gacggtacac tagtttacaa    1260
gtgtttttat atgttctaaa taaaattgag attttccgga acggtatgat ctgtttgcaa   1320
ataaggacgt atatataaca gtatcaaata tatttgttgt tataaggcaa taatatattt   1380
tctgagatat tgcgtgttac aaaaaagaaa tatttgttaa gaaaaaaaaa gatggtcgaa   1440 aaagggggagt aggtgggggc ggtcggcttt tgattagtta ataaaagaaa ccacacgagt   1500
gacctaccga ttcgactcaa cgagtctacc gagctaacac agattcaact cgctcgagct   1560
tcgttttatg acaagttggt ttttttttt tttttttaat ttttttcatct tcttgggttt    1620 ggttgggtca ctcttcaggt caggtgtgta aaaagaaag aaagaaaaga gagattgttg    1680
tgttgtaacc cctttgacta aaatctaatg aacttttta acacaacaaa actccttcag    1740
atctgaaagg gttcttcttc tctcttagtc tctttgtcct tttattctcc gtcgtcgttt   1800
catgatctga ctctctggtc ttctcttctt cttcttcttc ttctattttt tcttacttcg   1860
tcactgttgt gtctgaacat gccacgccct ttcttccata agttgatttt ctcatccact   1920
atccaagaaa aacgtctggt aacttactct ctctctctct ctctctctct gttctccttc   1980
tcctcatctt tcaaagtttt gattttgtgc gaaattgagg gttttcaagg tttggaatct   2040
ggtgaacgag tttgtaagat tatgccttgt gacactcttg cttgatttct tacaattcac   2100
ttgtattgat tctttgtaag aatcgagtca aggttgtgct tttatcttct tactcttccc   2160
tgttttgggt aatgaaaaga agttccattt ttgaactttg tgttgtctta ttggtcaaat   2220 gagaaatttgt gggtttccaa tggaagtctg caagacagtt tcttttggtc attggttgtg   2280
tttggtggga aattgggtat ttgatggtat atctgtactc tgacagcata ttgtgtgtag   2340
tttgggaatt tttttttttt ttttgagtga tttgactttt ggaggacgat ttgattctgt   2400
cagattgatc aaatttcttc tgaggagaaa aagttgagat ctgtttatgg tttctctatt   2460
ataaatgtct gttttgttta ctctattttg actgttttct ctgtttgact taggaatgtc   2520
tgagatctta gactccttat tgagtattgt gtggcttgtg agtgaatccc taaaactgag   2580
tagttgactt gttttgaagg tctctatgta ttgtgcttat gttttaaagt tgtctacttt    2640
atttgataca gtgattagtc atcacttgta cagattcccc caagagcatt gttttgaaca   2700
aatccaaatt tgcttagctc tccatttggc atttaagtga ctagattttc tctggaataa   2760
tgatttcgat taacacaggc atttatgtgg aaccaagttt gcaaattatt aatgtgataa   2820
```

```
gatcatagga gtcgtgtaat caatctattc agagataaat gtaccatttt acatgtgtac    2880
taatggactg tgtctccttg ttgatgcctt ctctaaactg aaatatggcc ttttggtttg    2940 tgttttttaaa ttaggtaaag ccgtcgtttc ttcagctact gtgtttattg gatgtttttg    3000
ctgaaaaatg tctgtttcga tttgatgttc tcgcaatatt ctgtgctgtt cttatagata    3060
ttgtggacat ttatatcatt atatgcttct ttatatctca taccggcatg cttgtgcaga    3120
gggtcccaga taagtttgtg agtaaattca aggatgagct ttcggttgct gttgcactca    3180
cagtacctga tggtcatgtt tgrcgtgtag gactaaggaa agctgacaac aaaatttggt    3240
ttcaagatgg ttggcaagag tttgttgacc gttactccat tcgcattggt tatcttttga    3300
tttttagata tgaaggaaac tctgccttca gcgtctacat tttcaattta tcccactctg    3360
agatcaatta ccattccacc ggtctcatgg attccgctca caaccacttc aaacgcgccc    3420
gtttgtttga agaccttgaa gatgaagatg ccgaggtcat cttccttct tctgtgtacc    3480 catcaccact tcctgagtct acagtaccag ccaacaaagg gtatgctagt tcagccatcc    3540
aaaccttgtt cactggacca gttaaaggtg atatttataa ccaactgatt ccctttatct    3600
atcgctgatt acgcgtctta tcattctttt gaggttgatg cttgatattt tccttatctc    3660
cagctgaaga gccaacgcca accccaaaaa tacctaaaaa gagagggagg aagaagaaaa    3720
atgctgatcc tggtaagcac ttttcctctt tgaaatgctt cagactcgtt ttcagaggat    3780
tcacagattc ttcctcatga tacatatatc cttttgatat tgtccttaca gaggaaataa    3840
actcatcagc tccgcgagat gatgatccag agaaccgttc aaagttctac gagagtgctt    3900
ctgcgagaaa gagaaccgtg actgcagaag aaagagagag agccatcaat gcagccaaaa    3960
cgttcgaacc aacaaaccct tcttcagag tggttctgcg accatcctat ctatacagag    4020
gttgcatcat ggtaataaaa aaacatctta ggaagactta atcttatcgg tgtcttcact    4080
gatctctaaa agaagccttc tgtttctgtt tctctcaaca gtatcttcct tctgggtttg    4140
ctgagaagta cctaagtggg atctccgggt tcatcaaagt ccagcttgcg gagaaacaat    4200
ggcctgttcg atgtctctac aaagccggga gagccaaatt cagtcaagga tggtacgaat    4260
tcactctaga gaacaactta ggagaaggag acgtctgtgt gtttgagctg ctcagaacca    4320
gagatttcgt tttgaaagtg acagcctttc gagtcaacga gtacgtctga acaaagcatt    4380
atggtgtgat cattctggat ttgcaagtac aatgtcgtgt aggagtatct taatttaaaa    4440
acaactaaaa aactctcttc tggtctgtgt cattattgcg tcagtgtctc gtttttctc    4500 tcgggtttac tttgtgttat cgatgtggat aagttgtttt tacctcatta tatataaccct    4560 cttgagtgga actcaaattg tttgagtaga acaaacaaag ttagggttta agaagaagtc    4620
tgtaaatacc taatctccat caaatttgag tagaaagaca aactgttctg gtggaataca    4680
aggagggaac ttgagataac aaacttaaga atagccttca agccaacgtc tagaatttga    4740
tgaagttgtt gtttgatcac ctctgagata attggaaacc ctcttcatgc agtttgcttg    4800
aggatactgg tgaaaatggg agtattgaag gaaaatgcat atataagatt gtaggtggga    4860
actgtggtag cagacacaac acttgttctc tagacatata ctgtaccaga catgttttga    4920
tcataaaact taaaaaaaag aaaaccgtgt gtaaatcaag caaggaacaa ctacaatatt    4980
acaatcttat tgagatatca                                                5000
```

<210> SEQ ID NO 2
<211> LENGTH: 27
<212> TYPE: DNA

```
<213> ORGANISM: Arabidopsis thaliana
<220> FEATURE:
<221> NAME/KEY: CDS
<222> LOCATION: (1)..(27)

<400> SEQUENCE: 2 gat ggt cat gtt tgg cgt gta gga cta                                27
Asp Gly His Val Trp Arg Val Gly Leu
 1               5

<210> SEQ ID NO 3
<211> LENGTH: 9
<212> TYPE: PRT
<213> ORGANISM: Arabidopsis thaliana

<400> SEQUENCE: 3

Asp Gly His Val Trp Arg Val Gly Leu
 1               5

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: vrn1-1
      mutation
<220> FEATURE:
<221> NAME/KEY: CDS
<222> LOCATION: (1)..(15)

<400> SEQUENCE: 4 gat ggt cat gtt tga cgtgtaggac ta                                  27
Asp Gly His Val
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: vrn1-2
      mutation

<400> SEQUENCE: 5

Asp Gly His Val
 1

<210> SEQ ID NO 6
<211> LENGTH: 27
<212> TYPE: DNA
<213> ORGANISM: Arabidopsis thaliana
<220> FEATURE:
<221> NAME/KEY: CDS
<222> LOCATION: (1)..(27)

<400> SEQUENCE: 6 aag aaa aat gct gat cct gag gaa ata                                27
Lys Lys Asn Ala Asp Pro Glu Glu Ile
 1               5

<210> SEQ ID NO 7
<211> LENGTH: 9
<212> TYPE: PRT
<213> ORGANISM: Arabidopsis thaliana

<400> SEQUENCE: 7

Lys Lys Asn Ala Asp Pro Glu Glu Ile
 1               5
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: vrn1-2
    mutation
<220> FEATURE:
<221> NAME/KEY: CDS
<222> LOCATION: (1)..(27)

<400> SEQUENCE: 8

| aag | aaa | atg | ctg | atc | ctg | agg | aaa | taa | | 27 |
|---|---|---|---|---|---|---|---|---|---|---|
| Lys | Lys | Met | Leu | Ile | Leu | Arg | Lys | | | |
| 1 | | | | 5 | | | | | | |

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: vrn1-2
    mutation

<400> SEQUENCE: 9

Lys Lys Met Leu Ile Leu Arg Lys
 1               5

<210> SEQ ID NO 10
<211> LENGTH: 1495
<212> TYPE: DNA
<213> ORGANISM: Arabidopsis thaliana
<220> FEATURE:
<221> NAME/KEY: CDS
<222> LOCATION: (269)..(1294)

<400> SEQUENCE: 10

| tcttgggttt | ggttgggtca | ctcttcaggt | caggtgtgta | aaaagaaag | aaagaaaaga | 60 |
|---|---|---|---|---|---|---|
| gagattgttg | tgttgtaacc | cctttgacta | aaatctaatg | aacttttta | acacaacaaa | 120 |
| actccttcag | atctgaaagg | gttcttcttc | tctcttagtc | tctttgtcct | tttattctcc | 180 |
| gtcgtcgttt | catgatctga | ctctctggtc | ttctcttctt | cttcttcttc | ttctattttt | 240 |

| tcttacttcg tcactgttgt gtctgaac atg cca cgc cct ttc ttc cat aag | 292 |
|---|---|
|                                            Met Pro Arg Pro Phe Phe His Lys | |
|                                            1               5 | |

| ttg att ttc tca tcc act atc caa gaa aaa cgt ctg agg gtc cca gat | 340 |
|---|---|
| Leu Ile Phe Ser Ser Thr Ile Gln Glu Lys Arg Leu Arg Val Pro Asp | |
| 10                  15                  20 | |

| aag ttt gtg agt aaa ttc aag gat gag ctt tcg gtt gct gtt gca ctc | 388 |
|---|---|
| Lys Phe Val Ser Lys Phe Lys Asp Glu Leu Ser Val Ala Val Ala Leu | |
| 25                  30                  35                  40 | |

| aca gta cct gat ggt cat gtt tgg cgt gta gga cta agg aaa gct gac | 436 |
|---|---|
| Thr Val Pro Asp Gly His Val Trp Arg Val Gly Leu Arg Lys Ala Asp | |
|                45                  50                  55 | |

| aac aaa att tgg ttt caa gat ggt tgg caa gag ttt gtt gac cgt tac | 484 |
|---|---|
| Asn Lys Ile Trp Phe Gln Asp Gly Trp Gln Glu Phe Val Asp Arg Tyr | |
|                   60                  65                  70 | |

| tcc att cgc att ggt tat ctt ttg att ttt aga tat gaa gga aac tct | 532 |
|---|---|
| Ser Ile Arg Ile Gly Tyr Leu Leu Ile Phe Arg Tyr Glu Gly Asn Ser | |
|      75                  80                  85 | |

| gcc ttc agc gtc tac att ttc aat tta tcc cac tct gag atc aat tac | 580 |
|---|---|
| Ala Phe Ser Val Tyr Ile Phe Asn Leu Ser His Ser Glu Ile Asn Tyr | |
| 90                  95                  100 | |

| | | | | | | | | | | | | | | |
|---|---|---|---|---|---|---|---|---|---|---|---|---|---|---|
| cat | tcc | acc | ggt | ctc | atg | gat | tcc | gct | cac | aac | cac | ttc | aaa cgc gcc | 628 |
| His | Ser | Thr | Gly | Leu | Met | Asp | Ser | Ala | His | Asn | His | Phe | Lys Arg Ala | |
| 105 | | | | | 110 | | | | | 115 | | | 120 | |
| cgt | ttg | ttt | gaa | gac | ctt | gaa | gat | gaa | gat | gcc | gag | gtc | atc ttt cct | 676 |
| Arg | Leu | Phe | Glu | Asp | Leu | Glu | Asp | Glu | Asp | Ala | Glu | Val | Ile Phe Pro | |
| | | | | 125 | | | | | 130 | | | | 135 | |
| tct | tct | gtg | tac | cca | tca | cca | ctt | cct | gag | tct | aca | gta | cca gcc aac | 724 |
| Ser | Ser | Val | Tyr | Pro | Ser | Pro | Leu | Pro | Glu | Ser | Thr | Val | Pro Ala Asn | |
| | | | 140 | | | | | 145 | | | | | 150 | |
| aaa | ggg | tat | gct | agt | tca | gcc | atc | caa | acc | ttg | ttc | act | gga cca gtt | 772 |
| Lys | Gly | Tyr | Ala | Ser | Ser | Ala | Ile | Gln | Thr | Leu | Phe | Thr | Gly Pro Val | |
| | | 155 | | | | | 160 | | | | | 165 | | |
| aaa | gct | gaa | gag | cca | acg | cca | acc | cca | aaa | ata | cct | aaa | aag aga ggg | 820 |
| Lys | Ala | Glu | Glu | Pro | Thr | Pro | Thr | Pro | Lys | Ile | Pro | Lys | Lys Arg Gly | |
| | 170 | | | | | 175 | | | | | 180 | | | |
| agg | aag | aag | aaa | aat | gct | gat | cct | gag | gaa | ata | aac | tca | tca gct ccg | 868 |
| Arg | Lys | Lys | Lys | Asn | Ala | Asp | Pro | Glu | Glu | Ile | Asn | Ser | Ser Ala Pro | |
| 185 | | | | | 190 | | | | | 195 | | | 200 | |
| cga | gat | gat | gat | cca | gag | aac | cgt | tca | aag | ttc | tac | gag | agt gct tct | 916 |
| Arg | Asp | Asp | Asp | Pro | Glu | Asn | Arg | Ser | Lys | Phe | Tyr | Glu | Ser Ala Ser | |
| | | | | 205 | | | | | 210 | | | | 215 | |
| gcg | aga | aag | aga | acc | gtg | act | gca | gaa | gaa | aga | gag | aga | gcc atc aat | 964 |
| Ala | Arg | Lys | Arg | Thr | Val | Thr | Ala | Glu | Glu | Arg | Glu | Arg | Ala Ile Asn | |
| | | 220 | | | | | 225 | | | | | 230 | | |
| gca | gcc | aaa | acg | ttc | gaa | cca | aca | aac | cct | ttc | ttc | aga | gtg gtt ctg | 1012 |
| Ala | Ala | Lys | Thr | Phe | Glu | Pro | Thr | Asn | Pro | Phe | Phe | Arg | Val Val Leu | |
| | 235 | | | | | 240 | | | | | 245 | | | |
| cga | cca | tcc | tat | cta | tac | aga | ggt | tgc | atc | atg | tat | ctt | cct tct ggg | 1060 |
| Arg | Pro | Ser | Tyr | Leu | Tyr | Arg | Gly | Cys | Ile | Met | Tyr | Leu | Pro Ser Gly | |
| 250 | | | | | 255 | | | | | 260 | | | | |
| ttt | gct | gag | aag | tac | cta | agt | ggg | atc | tcc | ggg | ttc | atc | aaa gtc cag | 1108 |
| Phe | Ala | Glu | Lys | Tyr | Leu | Ser | Gly | Ile | Ser | Gly | Phe | Ile | Lys Val Gln | |
| 265 | | | | 270 | | | | | 275 | | | | 280 | |
| ctt | gcg | gag | aaa | caa | tgg | cct | gtt | cga | tgt | ctc | tac | aaa | gcc ggg aga | 1156 |
| Leu | Ala | Glu | Lys | Gln | Trp | Pro | Val | Arg | Cys | Leu | Tyr | Lys | Ala Gly Arg | |
| | | | | 285 | | | | | 290 | | | | 295 | |
| gcc | aaa | ttc | agt | caa | gga | tgg | tac | gaa | ttc | act | cta | gag | aac aac tta | 1204 |
| Ala | Lys | Phe | Ser | Gln | Gly | Trp | Tyr | Glu | Phe | Thr | Leu | Glu | Asn Asn Leu | |
| | | | 300 | | | | | 305 | | | | | 310 | |
| gga | gaa | gga | gac | gtc | tgt | gtg | ttt | gag | ctg | ctc | aga | acc | aga gat ttc | 1252 |
| Gly | Glu | Gly | Asp | Val | Cys | Val | Phe | Glu | Leu | Leu | Arg | Thr | Arg Asp Phe | |
| | | 315 | | | | | 320 | | | | | 325 | | |
| gtt | ttg | aaa | gtg | aca | gcc | ttt | cga | gtc | aac | gag | tac | gtc | tga | 1294 |
| Val | Leu | Lys | Val | Thr | Ala | Phe | Arg | Val | Asn | Glu | Tyr | Val | | |
| | 330 | | | | | 335 | | | | | 340 | | | | acaaagcatt atggtgtgat cattctggat ttgcaagtac aatgtcgtgt aggagtatct    1354 taatttaaaa acaactaaaa aactctcttc tggtctgtgt cattattgcg tcagtgtctc    1414 gttttttctc tcgggtttac tttgtgttat cgatgtggat aagttgtttt tacctcatta    1474 tatataacct cttgagtgga a    1495

<210> SEQ ID NO 11
<211> LENGTH: 341
<212> TYPE: PRT
<213> ORGANISM: Arabidopsis thaliana

<400> SEQUENCE: 11

Met Pro Arg Pro Phe Phe His Lys Leu Ile Phe Ser Ser Thr Ile Gln
1               5              10            15

Glu Lys Arg Leu Arg Val Pro Asp Lys Phe Val Ser Lys Phe Lys Asp
            20                  25                  30

Glu Leu Ser Val Ala Val Ala Leu Thr Val Pro Asp Gly His Val Trp
        35                  40                  45

Arg Val Gly Leu Arg Lys Ala Asp Asn Lys Ile Trp Phe Gln Asp Gly
    50                  55                  60

Trp Gln Glu Phe Val Asp Arg Tyr Ser Ile Arg Ile Gly Tyr Leu Leu
65                  70                  75                  80

Ile Phe Arg Tyr Glu Gly Asn Ser Ala Phe Ser Val Tyr Ile Phe Asn
                85                  90                  95

Leu Ser His Ser Glu Ile Asn Tyr His Ser Thr Gly Leu Met Asp Ser
            100                 105                 110

Ala His Asn His Phe Lys Arg Ala Arg Leu Phe Glu Asp Leu Glu Asp
        115                 120                 125

Glu Asp Ala Glu Val Ile Phe Pro Ser Ser Val Tyr Pro Ser Pro Leu
    130                 135                 140

Pro Glu Ser Thr Val Pro Ala Asn Lys Gly Tyr Ala Ser Ser Ala Ile
145                 150                 155                 160

Gln Thr Leu Phe Thr Gly Pro Val Lys Ala Glu Pro Thr Pro Thr
                165                 170                 175

Pro Lys Ile Pro Lys Lys Arg Gly Arg Lys Lys Asn Ala Asp Pro
            180                 185                 190

Glu Glu Ile Asn Ser Ser Ala Pro Arg Asp Asp Pro Glu Asn Arg
        195                 200                 205

Ser Lys Phe Tyr Glu Ser Ala Ser Ala Arg Lys Arg Thr Val Thr Ala
    210                 215                 220

Glu Glu Arg Glu Arg Ala Ile Asn Ala Ala Lys Thr Phe Glu Pro Thr
225                 230                 235                 240

Asn Pro Phe Phe Arg Val Val Leu Arg Pro Ser Tyr Leu Tyr Arg Gly
                245                 250                 255

Cys Ile Met Tyr Leu Pro Ser Gly Phe Ala Glu Lys Tyr Leu Ser Gly
            260                 265                 270

Ile Ser Gly Phe Ile Lys Val Gln Leu Ala Glu Lys Gln Trp Pro Val
        275                 280                 285

Arg Cys Leu Tyr Lys Ala Gly Arg Ala Lys Phe Ser Gln Gly Trp Tyr
    290                 295                 300

Glu Phe Thr Leu Glu Asn Asn Leu Gly Glu Gly Asp Val Cys Val Phe
305                 310                 315                 320

Glu Leu Leu Arg Thr Arg Asp Phe Val Leu Lys Val Thr Ala Phe Arg
                325                 330                 335

Val Asn Glu Tyr Val
            340

<210> SEQ ID NO 12
<211> LENGTH: 1495
<212> TYPE: DNA
<213> ORGANISM: Artificial Sequence
<220> FEATURE:
<223> OTHER INFORMATION: Description of Artificial Sequence: vrn1-1
     mutation

<400> SEQUENCE: 12
tcttgggttt ggttgggtca ctcttcaggt caggtgtgta aaaagaaaag aaagaaaaga    60
gagattgttg tgttgtaacc cctttgacta aaatctaatg aacttttta acacaacaaa   120

-continued

```
actccttcag atctgaaagg gttcttcttc tctcttagtc tctttgtcct tttattctcc      180
gtcgtcgttt catgatctga ctctctggtc ttctcttctt cttcttcttc ttctattttt      240
tcttacttcg tcactgttgt gtctgaacat gccacgccct tcttccata agttgatttt       300 ctcatccact atccaagaaa aacgtctgag ggtcccagat aagtttgtga gtaaattcaa      360
ggatgagctt tcggttgctg ttgcactcac agtacctgat ggtcatgttt gacgtgtagg      420
actaaggaaa gctgacaaca aaatttggtt tcaagatggt tggcaagagt ttgttgaccg      480
ttactccatt cgcattggtt atcttttgat ttttagatat gaaggaaact ctgccttcag      540
cgtctacatt ttcaatttat cccactctga gatcaattac cattccaccg gtctcatgga     600
ttccgctcac aaccacttca aacgcgcccg tttgtttgaa gaccttgaag atgaagatgc      660
cgaggtcatc tttccttctt ctgtgtaccc atcaccactt cctgagtcta cagtaccagc     720
caacaaaggg tatgctagtt cagccatcca aaccttgttc actggaccag ttaaagctga     780
agagccaacg ccaaccccaa aaatacctaa aagagaggg aggaagaaga aaaatgctga     840
tcctgaggaa ataaactcat cagctccgcg agatgatgat ccagagaacc gttcaaagtt      900
ctacgagagt gcttctgcga gaaagagaac cgtgactgca gaagaaagag agagagccat     960
caatgcagcc aaaacgttcg aaccaacaaa ccctttcttc agagtggttc tgcgaccatc     1020
ctatctatac agaggttgca tcatgtatct tccttctggg tttgctgaga agtacctaag     1080
tgggatctcc gggttcatca aagtccagct tgcggagaaa caatggcctg ttcgatgtct     1140
ctacaaagcc gggagagcca aattcagtca aggatggtac gaattcactc tagagaacaa     1200
cttaggagaa ggagacgtct gtgtgtttga gctgctcaga accagagatt tcgttttgaa     1260
agtgacagcc tttcgagtca acgagtacgt ctgaacaaag cattatggtg tgatcattct     1320
ggatttgcaa gtacaatgtc gtgtaggagt atcttaattt aaaaacaact aaaaaactct     1380
cttctggtct gtgtcattat tgcgtcagtg tctcgttttt tctctcgggt ttactttgtg     1440
ttatcgatgt ggataagttg ttttttacctc attatatata acctcttgag tggaa          1495
```

<210> SEQ ID NO 13
<211> LENGTH: 1494
<212> TYPE: DNA
<213> ORGANISM: Artificial Sequence
<220> FEATURE:
<223> OTHER INFORMATION: Description of Artificial Sequence: vrn1-2
    mutation

<400> SEQUENCE: 13

```
tcttgggttt ggttgggtca ctcttcaggt caggtgtgta aaaagaaag aaagaaaaga       60 gagattgttg tgttgtaacc cctttgacta aaatctaatg aacttttta acacaacaaa      120 actccttcag atctgaaagg gttcttcttc tctcttagtc tctttgtcct tttattctcc      180
gtcgtcgttt catgatctga ctctctggtc ttctcttctt cttcttcttc ttctattttt      240
tcttacttcg tcactgttgt gtctgaacat gccacgccct tcttccata agttgatttt       300 ctcatccact atccaagaaa aacgtctgag ggtcccagat aagtttgtga gtaaattcaa      360
ggatgagctt tcggttgctg ttgcactcac agtacctgat ggtcatgttt ggcgtgtagg     420
actaaggaaa gctgacaaca aaatttggtt tcaagatggt tggcaagagt ttgttgaccg      480
ttactccatt cgcattggtt atcttttgat ttttagatat gaaggaaact ctgccttcag      540
cgtctacatt ttcaatttat cccactctga gatcaattac cattccaccg gtctcatgga     600
ttccgctcac aaccacttca aacgcgcccg tttgtttgaa gaccttgaag atgaagatgc      660
```

```
cgaggtcatc tttccttctt ctgtgtaccc atcaccactt cctgagtcta cagtaccagc    720
caacaaaggg tatgctagtt cagccatcca aaccttgttc actggaccag ttaaagctga    780
agagccaacg ccaaccccaa aaatacctaa aagagaggg aggaagaaga aaatgctgat    840
cctgaggaaa taaactcatc agctccgcga gatgatgatc cagagaaccg ttcaaagttc    900
tacgagagtg cttctgcgag aaagagaacc gtgactgcag aagaaagaga gagagccatc    960
aatgcagcca aaacgttcga accaacaaac cctttcttca gagtggttct gcgaccatcc   1020
tatctataca gaggttgcat catgtatctt ccttctgggt ttgctgagaa gtacctaagt   1080
gggatctccg ggttcatcaa agtccagctt gcggagaaac aatggcctgt tcgatgtctc   1140
tacaaagccg ggagagccaa attcagtcaa ggatggtacg aattcactct agagaacaac   1200
ttaggagaag gagacgtctg tgtgtttgag ctgctcagaa ccagagattt cgttttgaaa   1260
gtgacagcct ttcgagtcaa cgagtacgtc tgaacaaagc attatggtgt gatcattctg   1320
gatttgcaag tacaatgtcg tgtaggagta tcttaattta aaaacaacta aaaaactctc   1380
ttctggtctg tgtcattatt gcgtcagtgt ctcgttttt ctctcgggtt tactttgtgt   1440
tatcgatgtg gataagttgt ttttacctca ttatatataa cctcttgagt ggaa          1494
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
acctgcttct gccaaccgct c                                              21

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
agttcgctct tgctgttttt tttccc                                         26

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
cctcttcgct attacgccag                                                20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
gcccttccca acagttcg                                                  18

<210> SEQ ID NO 18
<211> LENGTH: 18

```
<212> TYPE: DNA
<213> ORGANISM: Artificial Sequence
<220> FEATURE:
<223> OTHER INFORMATION: Description of Artificial Sequence: Primer

<400> SEQUENCE: 18
cacacaggaa acagctat                                              18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
acacaacata cgagccggaa                                            20

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
caacggttag cccaaac                                               17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gtttgggcta accgttg                                               17

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
gagaccagtt ttgttttcc                                             19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
gacaaatata ggtggaaagg                                            20

<210> SEQ ID NO 24
<211> LENGTH: 17
<212> TYPE: DNA
<213> ORGANISM: Artificial Sequence
<220> FEATURE:
```

```
<223> OTHER INFORMATION: Description of Artificial Sequence:
      Oligonucleotide

<400> SEQUENCE: 24 aaagggagt aggtggg                                                    17

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
ctctctggtc ttctcttc                                                  18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
gaagagaaga ccagagag                                                  18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ttttctcatc cactatcc                                                  18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
tttcttggat agtggatgag                                                20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
aaaacaggga agagtaagaa g                                              21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
```

Oligonucleotide

<400> SEQUENCE: 30
cattggttgt gtttggtggg                                                 20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ggtctctatg tattgtgc                                                   18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
gcacaataca tagagacc                                                   18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
agattgatta cacgactcc                                                  19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
cccagataag tttgtgag                                                   18

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
attccgctca caaccac                                                    17

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 36
gtttgaagtg gttgtgag                                             18

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
tacccatcac cacttcc                                              17

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
cagaagaagg aaagatgacc                                           20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
gaagaaagag agagagcc                                             18

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
accctttctt cagagtg                                              17

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
ctctctctct ttcttctg                                             18

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide
```

```
<400> SEQUENCE: 42
ccactctgaa gaaaggg                                                  17

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
ccttctgttt ctgtttctc                                                19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
gagaaacaga aacagaagg                                                19

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
aagatactcc tacacgac                                                 18

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
gtctcgtttt ttctctcgg                                                19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
ctaccacagt tcccacctac                                               20

<210> SEQ ID NO 48
<211> LENGTH: 301
<212> TYPE: PRT
<213> ORGANISM: Arabidopsis thaliana

<400> SEQUENCE: 48

Met Pro Arg Ser Phe Phe His Met Phe Asn Ser Leu Phe Leu Ser Ser
 1               5                  10                  15
```

```
Thr Gln Ala Ser Gly Leu Arg Lys Ala Asn Asn Lys Ile Trp Phe Gln
             20                  25                  30
Asp Gly Trp Gln Glu Phe Val Asn Arg Phe Ser Ile Arg Ile Gly Phe
         35                  40                  45
Arg Tyr Lys Val Thr Val Tyr Ile Phe Gln Phe Tyr Pro Pro His Ser
     50                  55                  60
Glu Ile Asn His His Ser Ser Ser Glu Ala Leu Met Gln Met Asp Ser
 65                  70                  75                  80
Ala Gln Asn Gln Phe Asn Lys Arg Ala Arg Leu Phe Glu Asp Pro Glu
             85                  90                  95
Leu Lys Asp Ala Lys Val Ile Tyr Pro Ser Asn Pro Glu Ser Thr Glu
            100                 105                 110
Pro Val Asn Lys Gly Tyr Gly Gly Ser Thr Ala Ile Gln Ser Phe Phe
            115                 120                 125
Lys Glu Ser Lys Ala Glu Glu Thr Pro Lys Val Leu Lys Lys Arg Gly
        130                 135                 140
Arg Lys Lys Lys Asn Pro Asn Pro Glu Glu Val Asn Ser Ser Thr Pro
145                 150                 155                 160
Gly Gly Asp Asp Ser Glu Asn Arg Ser Lys Phe Tyr Glu Ser Ala Ser
                165                 170                 175
Ala Arg Lys Arg Thr Val Thr Ala Glu Glu Arg Glu Arg Ala Val Asn
            180                 185                 190
Ala Ala Lys Thr Phe Glu Pro Thr Asn Pro Tyr Phe Arg Val Val Leu
        195                 200                 205
Arg Pro Ser Tyr Leu Tyr Arg Gly Cys Ile Met Tyr Leu Pro Ser Gly
210                 215                 220
Phe Ala Glu Lys Tyr Leu Ser Gly Ile Ser Gly Phe Ile Lys Leu Gln
225                 230                 235                 240
Leu Gly Glu Lys Gln Trp Pro Val Arg Cys Leu Tyr Lys Ala Gly Arg
                245                 250                 255
Ala Lys Phe Ser Gln Gly Trp Tyr Glu Phe Thr Leu Glu Asn Asn Ile
            260                 265                 270
Gly Glu Gly Asp Val Cys Val Phe Glu Leu Leu Arg Thr Arg Asp Phe
        275                 280                 285
Val Leu Glu Val Thr Ala Phe Arg Val Asn Glu Tyr Val
290                 295                 300
```